United States Patent [19]

Achard et al.

[11] Patent Number: 5,451,601
[45] Date of Patent: Sep. 19, 1995

[54] PERHYDROISOINDOLE DERIVATIVES AND PHARMACEUTICAL COMPOSITIONS CONTAINING THEM

[75] Inventors: Daniel Achard, Thiais; Serge Grisoni, Choisy-le-Roi, both of France; Stephen Hanessian, Beaconsfields, Canada; Claude Moutonnier, Le Plessis Robinson, France; Jean-Francois Peyronel, Palaiseau, France; Michel Tabart, Paris, France; Alain Truchon, Lyons, France

[73] Assignee: Rhone-Poulenc Rorer S.A., Antony, France

[21] Appl. No.: 146,143

[22] PCT Filed: May 15, 1992

[86] PCT No.: PCT/FR92/00429

§ 371 Date: Nov. 17, 1993

§ 102(e) Date: Nov. 17, 1993

[87] PCT Pub. No.: WO92/20653

PCT Pub. Date: Nov. 26, 1992

[30] Foreign Application Priority Data

May 17, 1991 [FR] France ................. 91 06035

[51] Int. Cl.⁶ .................. A61K 31/40; C07D 209/08
[52] U.S. Cl. ..................... 514/416; 514/323; 546/200; 546/201; 548/465; 548/470; 548/515
[58] Field of Search ............ 548/465, 470, 515; 514/416, 323; 546/200, 201

[56] References Cited

U.S. PATENT DOCUMENTS 5,102,667  4/1992  Dubroeucq et al. ............... 424/489
5,112,988  5/1992  Dubroeucq et al. ............... 548/470

FOREIGN PATENT DOCUMENTS 0429366  5/1991  European Pat. Off. .
0430771  6/1991  European Pat. Off. .
514274  11/1992  European Pat. Off. ............ 548/470

OTHER PUBLICATIONS

Lotz, M. et al, "Effect of Neuropeptides on Production of Inflammatory Cytokines by Human Monocytes," Science, vol. 241, p. 1218, Sep. 1988.

Primary Examiner—Jacqueline Haley
Attorney, Agent, or Firm—Morgan & Finnegan

[57] ABSTRACT

This invention relates to derivatives of perhydroisoindol of formula:

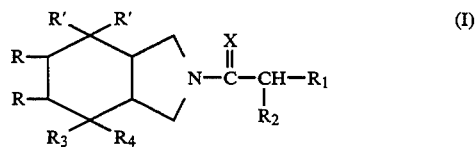

in which the radicals R are hydrogen atoms or together form a bond, the symbols R' are phenyl radicals which can be substituted by a halogen atom or a methyl radical in position 2 or 3, X is an oxygen atom or an NH radical, $R_1$ is optionally substituted phenyl, or cyclohexadienyl, naphthyl, or heterocyclyl, $R_2$ is H, halogen, OH, alkyl, aminoalkyl, alkylaminoalkyl, dialkylaminoalkyl, alkyloxy, alkylthio, acyloxy, carboxy, optionally substituted alkyloxycarbonyl, benzyloxycarbonyl, amino or acylamino, $R_3$ is halogen or OH and $R_4$ is H or halogen if $R_3$ is halogen, in their isomer forms, or mixture thereof, and possibly also their salts when they exist, and preparation thereof. The derivatives of the invention are particularly interesting as P substance antagonist.

9 Claims, No Drawings

PERHYDROISOINDOLE DERIVATIVES AND PHARMACEUTICAL COMPOSITIONS CONTAINING THEM

This application is a National Stage Application of PCT/FR92/00429, filed May 15, 1992, now WO 92/20653, published Nov. 26, 1992.

FIELD OF THE INVENTION

The present invention relates to new perhydroisoindole derivatives of the general formula:

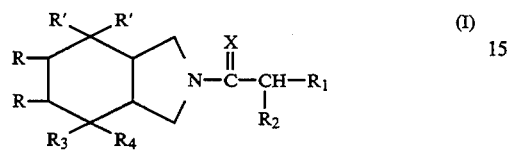

and their salts when these exist, which antogonise the effects of the substance P and are as a result particularly useful in the therapeutic sectors where this substance is known to play a role.

BACKGROUND OF THE INVENTION

Products derived from the isoindole of the general formula:

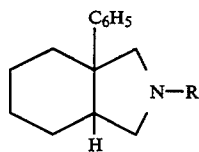

which exhibit opium activity, had been described in U.S. Pat. No. 4,042,707.

These products exhibit no activity towards substance P.

In spite of the research carried out and in spite of the interest created [M. R. Hanley, TINS, (5) 139 (1982)], practically no product had been discovered so far which acts specifically on substance P and which has a nonpeptide structure; accordingly, the isoindole derivatives of general formula (I) are of great interest.

DESCRIPTION OF THE INVENTION

In the general formula (I):
the R radicals are identical and represent hydrogen atoms or together form a bond,
the symbols R' are identical and they represent phenyl radicals which are optionally substituted in position 2 or 3 by a halogen atom or by a methyl radical,
the symbol X represents an oxygen atom or an NH radical,
the symbol $R_1$ represents a phenyl radical which is optionally substituted by one or more halogen atoms or hydroxyl or alkyl radicals which may be optionally substituted (by halogen atoms or amino, alkylamino or dialkylamino radicals) alkoxy or alkylthio radicals which may be optionally substituted [by hydroxyl, amino, alkylamino or dialkylamino radicals optionally substituted (by phenyl, hydroxyl or amino radicals) or by dialkylamino radicals whose alkyl parts form with the nitrogen atom to which they are attached, a heterocycle with 5 to 6 members which may contain another heteroatom chosen from oxygen, sulphur or nitrogen, optionally substituted by an alkyl, hydroxyl or hydroxyalkyl radical)], or which is substituted by amino, alkylamino or dialkylamino radicals whose alkyl parts may form with the nitrogen atom to which they are attached, a heterocycle as defined above, or represents a cyclohexadienyl, naphthyl or a saturated or unsaturated, mono- or polycyclic heterocyclic radical containing 5 to 9 carbon atoms and one or more heteroatoms chosen from oxygen, nitrogen or sulphur, the symbol $R_2$ represents a hydrogen or halogen atom or a hydroxyl, alkyl, aminoalkyl, alkylaminoalkyl, dialkylaminoalkyl, alkoxy, alkylthio, acyloxy, carboxyl, alkoxycarbonyl, dialkylaminoalkoxycarbonyl, benzyloxycarbonyl, amino, acylamino or alkoxycarbonylamino radical, the symbol $R_3$ represents a halogen atom or a hydroxyl radical, and the symbol $R_4$ represents a hydrogen atom or, together with $R_3$, represents a halogen atom.

It is understood that the abovementioned alkyl or acyl radicals contain 1 to 4 carbon atoms in a linear or branched chain.

When R' carries a halogen substituent, the latter may be chosen from chlorine or fluorine.

When $R_1$ contains a halogen atom, the latter may be chosen from chlorine, bromine, fluorine or iodine.

When $R_1$ represents a saturated or unsaturated, mono- or polycyclic heterocyclic radical, it may for example be chosen from thienyl, furyl, pyridyl, dithiinyl, indolyl, isoindolyl, thiazolyl, isothiazolyl, oxazolyl, imidazolyl, pyrrolyl, triazolyl, thiadiazolyl, quinolyl, isoquinolyl or naphthyridinyl.

When $R_1$ represents a phenyl which is substituted by a chain carrying a heterocycle, the latter may be chosen from pyrrolidinyl, morpholino, piperidinyl, tetrahydropyridinyl, piperazinyl or thiomorpholino.

When $R_3$ is a halogen atom, it may be advantageously chosen from fluorine or chlorine.

Moreover, the products of general formula (I) have various stereoisomeric forms, it is understood that the isoindole derivatives of the (3aR,7aR) form, in the pure state, or in the form of a mixture of the cis-(3aRS,7aRS) forms, are included within the scope of the present invention. When the radicals $R_3$ and $R_4$ are different, it is also understood that the substituent R3 may be in the axial or equatorial position and, therefore, that the R and S derivatives and mixtures thereof are also included within the scope of the present invention. Furthermore, when the symbol $R_2$ is other than the hydrogen atom, the substituted chain on the isoindole has a chiral centre, it is understood that the stereoisomeric forms and mixtures thereof are also included within the scope of the present invention.

According to the invention, the perhydroisoindole derivatives of general formula (I) may be obtained by reaction of the acid of general formula:

or of a reactive derivative of this acid, in which $R_1$ and $R_2$ are defined as above, with an isoindole derivative of general formula:

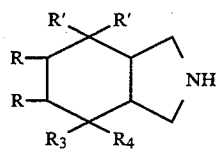

(III)

in which the symbols R, R', R₃ and R₄ are defined as above, followed, where appropriate, by conversion of the amide obtained to an amidine.

It is understood that the amino, alkylamino or carboxyl radicals contained in $R_1$ and/or $R_2$ are preferably protected beforehand. The protection is carried out using any compatible group whose introduction and removal does not affect the rest of the molecule. In particular the procedure is carried out according to the methods described by T. W. Greene, Protective Groups in Organic Synthesis, A. Wiley—Interscience Publication (1981), or by Mc Omie, Protective Groups in Organic Chemistry, Plenum Press (1973).

By way of example, the amino or alkylamino groups may be protected with the following radicals: methoxycarbonyl, ethoxycarbonyl, t-butoxycarbonyl, allyloxycarbonyl, vinyloxycarbonyl, trichloroethoxycarbonyl, trichloroacetyl, trifluoroacetyl, chloroacetyl, trityl, benzhydryl, benzyl, allyl, formyl, acetyl, benzyloxycarbonyl or its substituted derivatives;

the acidic groups may be protected with the following radicals: methyl, ethyl, t-butyl, benzyl, substituted benzyl or benzhydryl.

Furthermore, when $R_2$ represents a hydroxyl radical, it is preferable to protect this radical beforehand. The protection is carried out for example using an acetyl, trialkylsilyl or benzyl radical or in the form of a carbonate using a -COORa radical in which Ra is an alkyl or benzyl radical.

When the condensation of a reactive derivative of the acid of general formula (II) is carried out, the procedure is advantageously carried out using the acid chloride, the anhydride, a mixed anhydride or a reactive ester in which the ester residue is a succinimido, an optionally substituted 1-benzotriazolyl, a 4-nitrophenyl, a 2,4-dinitrophenyl, a pentachlorophenyl or a phthalimido radical.

The reaction is generally carried out at a temperature of between −40° and +40° C. in an organic solvent such as a chlorine-containing solvent (for example dichloromethane, dichloroethane, chloroform), a hydrocarbon (for example toluene), an ether (for example tetrahydrofuran, dioxane), an ester (for example ethyl acetate), an amide (for example dimethylacetamide, dimethylformamide), or a ketone (for example acetone) or in a mixture of these solvents, in the presence of an acid acceptor such as a nitrogen-containing organic base such as for example pyridine, dimethylaminopyridine, N-methylmorpholine or a trialkylamine (in particular triethylamine) or such as an epoxide (for example propylene oxide). It is also possible to carry out the procedure in the presence of a condensation agent such as a carbodiimide, [for example dicyclohexylcarbodiimide or 1-(3-dimethylaminopropyl)-3-ethylcarbodiimide], N,N'-carbonyldiimidazole or 2-ethoxy-1-ethoxycarbonyl-1,2-dihydroquinoline or alternatively in a dilute organic medium in the presence of an alkaline condensation agent such as sodium bicarbonate, and where appropriate the amide obtained is then converted to an amidine as defined above.

The conversion of the amide of general formula (I) to an amidine for which X is an NH radical is carried out by preparing the isoindolium derivative of general formula:

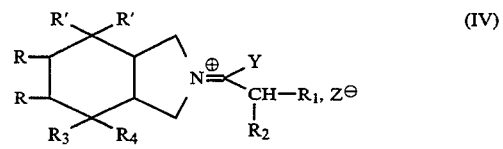

(IV)

in which R, R', $R_1$, $R_2$, $R_3$ and $R_4$ are defined as above, Y represents a chlorine atom, a methoxy or ethoxy radical and $Z^-$ represents a chloride, tetrafluoroborate, fluorosulphonate, trifluoromethylsulphonate, methyl sulphate or ethyl sulphate ion, and subsequently by reacting ammonia with the isoindolium derivative.

It is understood that when $R_3$ is a hydroxyl, Y is other than a chlorine atom.

The preparation of the isoindolium derivative of general formula (IV) in which Y is a chlorine atom or a methoxy or ethoxy radical, is carried out by reaction of a reagent such as phosgene, phosphorus oxychloride, phosphorus pentachloride, thionyl chloride, oxalyl chloride, trichloromethyl chloroformate, triethyl- or trimethyloxonium tetrafluoroborate, methyl or ethyl triflate, methyl or ethyl fluorosulphonate or methyl or ethyl sulphate. The reaction is carried out in a chlorine-containing solvent (for example dichloromethane, dichloroethane) or in an aromatic hydrocarbon (for example toluene) at a temperature between 0° C. and the reflux temperature of the reaction mixture. The reaction of ammonia with the derivative of general formula (IV) is carried out in an anhydrous organic solvent such as a chlorine-containing solvent (for example dichloromethane, dichloroethane) in an alcohol-chlorine-containing solvent mixture, in an ether (for example tetrahydrofuran), in an ester (for example ethyl acetate), in an aromatic solvent (for example toluene) or in a mixture of these solvents, at a temperature between −20° C. and the reflux temperature of the reaction mixture.

It is not essential to have isolated the isoindolium derivative of general formula (IV) in order to use it in this reaction.

According to the invention, the isoindole derivative of general formula (I), for which $R_3$ represents a halogen atom and $R_4$ represents a hydrogen atom, may also be obtained by halogenation of the corresponding derivative of the isoindole of general formula (I) for which $R_3$ is a hydroxyl radical, $R_4$ is a hydrogen atom and X is an oxygen atom, and where appropriate, then converting the amide obtained to an amidine.

When it is desired to obtain a product for which $R_3$ represents a fluorine atom, the reaction is advantageously carried out using a fluorinating agent such as a sulphur fluoride [morpholinosulphur trifluoride, sulphur tetrafluoride (J. Org. Chem., 40, 3808 (1975)), diethylaminosulphur trifluoride (Tetrahedron, 44, 2875 (1988)), phenylsulphur trifluoride (J. Am. Chem. Soc., 84, 3058 (1962)), such as hexafluoropropyldiethylamine (Japanese Patent 2,039,546) or N-(2-chloro1,1,2-trifluoroethyl)diethylamine, such as selenium tetrafluoride (J. Am. Chem. Soc., 96,925 (1974) or such as tetrafluorophenylphosphorane (Tet. Let., 907 (1973), by carrying out the procedure in an organic solvent such as a chlorine-containing solvent (for example dichloromethane, dichloroethane), at a temperature between −30° and 30° C. It is understood that the use of an alcohol of the (S) configuration leads to the fluorine-containing derivative of the (R) configuration and that the use of an alcohol of the (R) configuration leads to the fluorine-containing derivative of the (S) configuration.

When it is desired to obtain a product for which $R_3$ represents a chlorine atom, the chlorine-containing derivative of the (R) configuration may be obtained by treating the (S) alcohol with phosphorus pentachloride under the conditions defined by R. J. Cremlyn et al., J. Chem. Soc., 3794 (1954); the chlorine-containing derivative of the (S) configuration may be obtained by treating the (S) alcohol with thionyl chloride under the conditions stated by R. J. Cremlyn in the abovementioned reference.

According to the invention, the isoindole derivatives of general formula (I) for which $R_3$ is a hydroxyl radical and $R_4$ is a hydrogen atom, may also be obtained by reducing the isoindolone derivative of general formula:

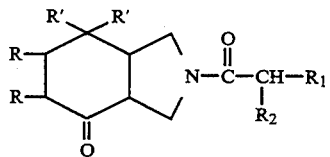

(V)

in which R, R', $R_1$ and $R_2$ are defined as above, followed by the separation of the axial and equatorial isomers and by the conversion of the amide obtained to an amidine.

The reduction is advantageously carried out using an alkali metal borohydride (sodium borohydride, lithium tri-s-butylborohydride) in a solvent such as an alcohol (for example methanol, ethanol) or an ether (tetrahydrofuran) in a basic medium, at a temperature between −20° and 50° C.

According to the invention, the isoindole derivatives of general formula (I) for which X is an imino radical, may also be obtained from the isoindole derivative of general formula (III), by reaction of a product of general formula:

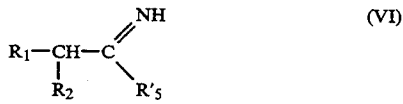

(VI)

optionally in the form of a salt, in which $R_1$ and $R_2$ are defined as above and $R'_5$ represents an alkoxy radical containing 1 to 4 carbon atoms in a linear or branched chain, or a methylthio, ethylthio, benzylthio or alkoxycarbonylmethylthio radical.

The reaction is carried out using the derivative of general formula (VI), which is optionally prepared in situ, in an organic solvent such as a chlorine-containing solvent (for example dichloromethane, dichloroethane), an ether (for example tetrahydrofuran), an aromatic hydrocarbon (for example toluene) or a nitrile, for example acetonitrile, at a temperature between 0° C. and the reflux temperature of the reaction fixture.

It is understood that should the radicals $R_1$ and/or $R_2$ of the product of general formula (VI) carry substituents which may interfere with the reaction, these substituents should be protected beforehand.

The acids of general formula (II) may be prepared according to the methods described below, in the examples, or by analogy with these methods.

The isoindole derivative of general formula (III) for which $R_3$ is a halogen atom and $R_4$ is a hydrogen or halogen atom, may be prepared by halogenation of an isoindole of the general formula:

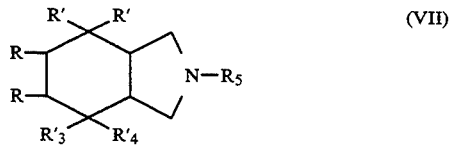

(VII)

in which R and R' are defined as above, $R_5$ is a protective radical, $R'_3$ is a hydroxyl radical and $R'_4$ a hydrogen atom if it is desired to obtain a monohalogenated isoindole derivative, or alterntively $R'_3$ and $R'_4$, together form an oxo radical if it is desired to obtain a dihalogenated isoindole derivative, followed by removal of the protective radical $R_5$.

The protective radical $R_5$ may be any amino-protecting group which is compatible with the reaction and whose introduction and removal does not affect the rest of the molecule. Alkoxycarbonyl groups, benzyloxycarbonyl groups, optionally substituted benzyl groups, formyl, chloroacetyl, trichloroacetyl, trifluoroacetyl, vinyloxycarbonyl, phenoxycarbonyl, 1-chloroethoxycarbonyl or chlorocarbonyl groups may be mentioned by way of example.

When it is desired to obtain a fluorine-containing perhydroisoindole derivative of general formula (III), the fluorination is carried out under the conditions described above for the fluorination of a derivative of general formula (I) in which $R_3$ is hydroxyl, at a temperature between −30° and +30° C. It is understood that the fluorine-containing derivative of the (R) configuration is obtained from an alcohol of the (S) configuration and that the fluorine-containing derivative of the (S) configuration is obtained from the hydroxylated derivative of the (R) configuration. It is also possible to carry out the procedure using a mixture of alcohols of the (R) and (S) configurations and to carry out the separation with respect to the derivative of general formula (III).

When it is desired to obtain the difluorine-containing derivative of general formula (III), the reaction is carried out using the isoindolone of general formula (VII) ($R'_3$ and $R'_4$, together, form an oxo radical), by carrying out the procedure under the conditions defined above, at a temperature between 30° C. and the reflux temperature of the reaction mixture.

When it is desired to obtain a chlorine-containing perhydroisoindole derivative of general formula (III), the chlorination is carried out according to the conditions described by R. J. Cremlyn et al., J. Chem. Soc., 3794 (1954), either by means of phosphorus pentachloride using the hydroxylated derivative of the (S) configuration when it is desired to obtain the chlorine-containing derivative of the (R) configuration, or by means of thionyl chloride using the hydroxylated derivative of the (S) configuration when it is desired to obtain a chlorine-containing derivative of the (S) configuration. It is understood that the separation may also be carried out with respect to the product of general formula (III).

When it is desired to obtain the dichlorine-containing derivative, the procedure is carried out using perhydroisoindole of general formula (VII), by treatment with phosphorus pentachloride under the conditions mentioned above.

Subsequent removal of the protective radical $R_5$ is carried out according to the usual methods, in particular according to the methods described by T. W. Greene, by A. Wiley or by Mc Omie in the abovementioned references.

The isoindole derivative of general formula (III) for which $R_3$ is a halogen atom and $R_4$ is a hydrogen atom, may also be obtained by halogenation of a perhydroisoindole derivative of general formula:

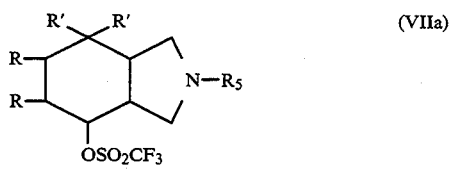

(VIIa)

in which R and R' are defined as above, followed by removal of the protective radical $R_5$.

The halogenation is carried out using a quaternary ammonium halide such as for example tetrabutylammonium fluoride or using an alkali metal halide such as for example potassium fluoride or caesium fluoride, in anhydrous medium, in an organic solvent such as an ether (for example tetrahydrofuran, dioxane), a chlorine-containing solvent (for example dichloromethane) or in a mixture of solvents, at a temperature between $-30°$ and $50°$ C.

It is understood that the sulphonylated derivative of general formula (VIIa) of the (S) configuration leads to a halogenated derivative of the (R) configuration and that the sulphonylated derivative of the (R) configuration leads to a halogenated derivative of the (S) configuration.

The removal of the radical $R_5$ is carried out as described above.

The sulphonylated derivative of general formula (VIIa) may be obtained by treating the perhydroisoindole derivative of general formula (VII), for which $R'_3$ is a hydroxyl radical and $R'_4$ is a hydrogen atom, with a reactive trifluoromethanesulphonic acid derivative.

The reaction is generally carried out by reaction of trifluoromethanesulphonic anhydride in the presence of pyridine, in a chlorine-containing solvent (for example dichloromethane), at a temperature of about $30°$ C.

The perhydroisoindole derivative of general formula (VII) may be prepared by protecting the amino of the corresponding derivative of general formula:

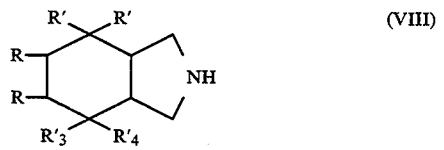

(VIII)

in which R, R', $R'_3$ and $R'_4$ are defined as for the general formula (VII).

The protection is carried out according to the usual methods, in particular according to the references mentioned above.

The perhydroisoindole derivative of general formula (VII) or (VIII), for which $R'_3$ is a hydroxyl radical and $R'_4$ is a hydrogen atom, may be obtained by reduction of the corresponding perhydroisoindole derivative of general formula (VII) or (VIII) for which $R'_3$ and $R'_4$, together, form an oxo radical The reduction is carried out under conditions similar to those described for the production of the perhydroisoindoles of general formula (I), for which $R_3$ is hydroxyl, from the corresponding perhydroisoindolone.

The hydroxylated perhydroisoindole derivative of general formula (III) or (VIII), for which $R'_3$ is a hydroxyl radical and $R'_4$ is a hydrogen atom, may be obtained by releasing the protective radical $R_5$ from the corresponding perhydroisoindole derivative of general formula (VII) in which $R'_3$ and $R'_4$ are defined as above.

The removal is carried out using known methods which do not affect the rest of the molecule.

The isoindole derivative of general formula (VIII), for which $R'_3$ and $R'_4$ together form an oxo radical, may be obtained from the corresponding derivative of general formula:

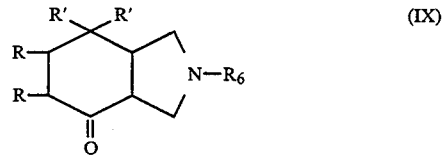

(IX)

in which R and R' are defined as above and $R_6$ represents an allyl radical or a radical of the structure $-CR_aR_bR_c$ in which $R_a$ and $R_b$ are hydrogen atoms or phenyl radicals which are optionally substituted (by a halogen atom, an alkyl, alkoxy or nitro radical), and $R_c$ is defined as $R_a$ and $R_b$ or represents an alkyl or alkoxyalkyl radical, at least one of $R_a$, $R_b$ and $R_c$ being a substituted or unsubstituted phenyl radical and the alkyl radicals containing 1 to 4 carbon atoms in a linear or branched chain, by removing the radical $R_6$ by any known method which does not affect the rest of the molecule.

In particular, when R is a hydrogen atom, and when $R_6$ is other than an allyl radical, the group $R_6$ may be removed by catalytic hydrogenation in the presence of palladium. Generally, the reaction is carried out in an acidic medium, in a solvent such as an alcohol (methanol, ethanol), in water or directly in acetic acid or formic acid, at a temperature between $20°$ and $60°$ C.

When $R_6$ is a benzhydryl or trityl radical, the removal may be carried out by treatment in an acidic medium, by carrying out the procedure at a temperature of between $0°$ C. and the reflux temperature of the reaction mixture, in an alcohol, in an ether, in water or directly in acetic acid, formic acid or trifluoroacetic acid. The group $R_6$ may also be removed by reaction of vinyl chloroformate, 1-chloroethyl chloroformate or phenyl chloroformate, a product of general formula:

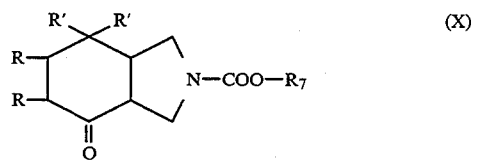

(X)

in which R and R' are defined as above, and $R_7$ is a vinyl, 1-chloroethyl or phenyl radical, being obtained as an intermediate, and then by removing the radical —COOR$_7$ by acid treatment. The reaction of the chloroformate is generally carried out in an organic solvent such as a chlorine-containing solvent (for example dichloromethane, dichloroethane, chloroform), an ether (for example tetrahydrofuran, dioxane) or a ketone (for example acetone) or in a mixture of these solvents, by carrying out the procedure at a temperature of between 20° C. and the reflux temperature of the reaction mixture.

The removal of the radical —COOR$_7$ is carried out by treatment in an acidic medium for example with trifluoroacetic, formic, methanesulphonic, p-toluenesulphonic, hydrochloric or hydrobromic acid in a solvent such as an alcohol, an ether, an ester, a nitrile, a mixture of these solvents or in water, at a temperature between 0° C. and the reflux temperature of the reaction mixture.

Under the conditions for removing the —COOR$_7$ radicals mentioned above, the isoindolone derivative of general formula (VIII) is obtained in the form of a salt of the acid used, which may be used directly in the subsequent stage.

The isoindolone derivative of general formula (IX) (or (VII) when R'$_3$ and R'$_4$ together form an oxo radical and R$_5$ is an optionally substituted benzyl radical), may be obtained by cycloaddition reaction, by reaction of a silylated derivative of general formula:

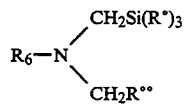

(XI)

in which R$_6$ is defined as above, (R°)$_3$ represents alkyl radicals or alkyl and phenyl radicals and R°° represents an alkoxy, cyano or phenylthio radical, with the cyclohexenone derivative of general formula:

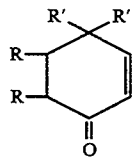

(XII)

in which R and R' are defined as above.

The procedure is carried out in the presence of a catalytic amount of an acid chosen from trifluoroacetic acid, acetic acid, methanesulphonic acid or the acids given in the references mentioned below, in an organic solvent such as a chlorine-containing solvent (for example dichloromethane, dichloroethane), in an aromatic hydrocarbon, in a nitrile (acetonitrile) or in an ether, at a temperature between 0° C. and the reflux temperature of the reaction mixture.

The silylated derivative of general formula (XI) may be obtained according to the methods described by:
Y. Terao et al., Chem. Pharm. Bull., 33, 2762 (1985);
A. Hosomi et al., Chem. Lett., 1117 (1984)
A. Padwa et al., Chem. Ber., 119, 813 (1986) or
Tetrahedron, 41, 3529 (1985).

It is understood that the perhydroisoindole derivatives of general formula (I), (III), (V), (VII), (VIIa), (VIII), (IX) and (X) have several stereoisomeric forms. When it is desired to obtain a product of general formula (I) of the (3aR,7aR) form, the separation of the isomeric forms is preferably carried out with respect to the derivative of general formula (VIII) for which R'$_3$ and R'$_4$ together form an oxo radical. It may also be carried out with respect to the derivative of general formula (III). The separation is carried out according to any known method which is compatible with the molecule.

By way of example, the separation may be carried out by the preparation of an optically active salt, by reaction of L(+) or D(−)-mandelic acid, or of dibenzoyltartaric acid, followed by separation of the isomers by crystallization. The desired isomer is released from its salt in a basic medium.

The separation of the axial and equatorial isomers of the hydroxylated derivatives or of the halogenated derivatives is advantageously carried out with respect to the products of general formula (VII) or (VIII), the procedure being carried out by crystallization and chromatography. It is also possible to carry out the procedure with respect to the products of general formula (III) or (I).

The new isoindole derivatives of general formula (I) may be purified, where appropriate, by physical methods such as crystallization or chromatography.

Where appropriate, the new derivatives of general formula (I), for which the symbols R$_1$ and/or R$_2$ contain amino or alkylamino substituents and/or X represents an NH radical, may be converted to the addition salts with acids. As examples of addition salts with pharmaceutically acceptable acids, there may be mentioned the salts formed with inorganic acids (hydrochlorides, hydrobromides, sulphates, nitrates, phosphates) or with organic acids (succinates, fumarates, tartrates, acetates, propionates, maleates, citrates, methanesulphonates, p-toluenesulphonates, isethionates, or with substituted derivatives of these compounds).

The new isoindole derivatives of general formula (I) may also, where appropriate, when R$_2$ represents a carboxyl radical, be converted to the metal salts or to the addition salts with a nitrogen-containing base, according to methods which are known per se. These salts may be obtained by reaction of a metal base (for example alkali metal or alkaline earth metal), of ammonia or an amine, with a product according to the invention, in an appropriate solvent such as an alcohol, an ether or water, or by exchange reaction with an organic acid salt. The salt formed precipitates after optional concentration of the solution, it is separated by filtration, decantation or freeze-drying. As examples of pharmaceutically acceptable salts, there may be mentioned salts with alkali metals (sodium, potassium, lithium) or with alkaline earth metals (magnesium, calcium), ammonium salt, salts of nitrogen-containing bases (ethanolamine, diethanolamine, trimethylamine, triethylamine, methylamine, propylamine, diisopropylamine, N,N-dimethylethanolamine, benzylamine, dicyclohexylamine, N-benzyl-β-phenethylamine, N,N'-dibenzylethylenediamine, diphenylenediamine, benzhyldrylamine, quinine, choline, arginine, lysine, leucine, dibenzylamine).

The new isoindole derivatives according to the present invention which antagonise the effects of substance P may find an application in the fields of analgesia, inflammation, asthma, allergies, on the central nervous system, on the cardiovascular system, as antispasmodic, or on the immune system, as well as in the domain of the stimulation of lachrymal secretions.

Indeed, the products according to the invention exhibit an affinity for substance P receptors at doses of between 5 and 2000 nM according to the technique described by C. M. Lee et al., Mol. Pharmacol., 23, 563–69 (1983).

Furthermore, it has been demonstrated, using various products, that it is a substance P-antagonizing effect. In the technique described by S. Rosell et al., Substance P, Ed. by US Von Euler and B. Pernow, Raven Press, New York (1977), pages 83 to 88, the products studied proved to be active at doses of between 20 and 1000 nM.

Substance P is known to be involved in a certain number of pathological domains:

Agonists and antagonists of substance P, A. S. Dutta Drugs of the future, 12 (8), 782 (1987);

Substance P and pain: an updating, J. L. Henry, TINS, 3(4), 97 (1980);

Substance P in inflammatory reactions and pain, S. Rosell, Actual. Chim. Ther., 12th series, 249 (1985);

Effects of Neuropeptides on Production of Inflammatory Cytokines by Human Monocytes, M. Lotz et al., Science, 241, 1218 (1988);

Neuropeptides and the pathogenesis of allergy, Allergy, 42, 1 to 11 (1987);

Substance P in Human Essential Hypertension, J. Cardiovascular Pharmacology, 10 (suppl. 12), 5172 (1987).

The study of a number of products has demonstrated in particular that the new isoindole derivatives exhibit an analgesic activity according to the technique of Siegmund E. et al., Proc. Soc. Exp. Biol. Med., 95, 729 (1957).

| Product of general formula (I) | $ED_{50}$ mg/kg p.o. |
|---|---|
| Example 1 | 3 |
| Example 2 | 2 |
| Example 7 | 1.5 |

The study of a number of isoindole derivatives of general formula (I) according to the technique of A. Saria et al., Arch. Pharmacol., 324, 212–218 (1983) adapted to mice, has made it possible to demonstrate an inhibitory effect of the increase in capillary permeability brought about by septide (agonist of substance P), which is evidence of an anti-inflammatory activity:

| Product of general formula (I) | $ED_{50}$ mg/kg s.c. |
|---|---|
| Example 1 | 0.70 |
| Example 2 | 0.30 |
| Example 7 | 0.32 |

Injection of substance P into animals produces hypotension. The products studied in the technique of C. A. Maggi et al., J. Auton. Pharmac., 7, 11–32 (1987) exhibit an antagonistic effect in rats towards this hypotension. In particular, the products administered at a dose of 1 mg/kg i.v./min, for 5 min, produce antagonism of the hypotension induced by an i.v. injection of 250 mg/kg of substance P.

| Product of general formula (I) | % inhibition of hypotension |
|---|---|
| Example 1 | 73 |
| Example 2 | 68 |

Moreover, the isoindole derivatives according to the present invention are not toxic, they proved to be non-toxic in mice by the subcutaneous route at a dose of 40 mg/kg or by the oral route at a dose of 100 mg/kg.

The products of general formula (I) in which:
the radicals R are hydrogen atoms,
the symbols R' are phenyl radicals,
the symbol X represents an oxygen atom or an NH radical,
the symbol $R_1$ represents a phenyl radical which is optionally substituted by an alkoxy radical which may be optionally substituted [by a dialkylamino radical or a dialkylamino radical whose alkyl parts form with the nitrogen atom to which they are attached, a heterocycle with 5 to 6 members], or substituted by a dialkylamino radical whose alkyl parts may form with the nitrogen atom to which they are attached, a heterocycle as defined above,
the symbol $R_2$ represents a hydrogen atom or an alkyl radical,
the symbol $R_3$ represents a fluorine or chlorine atom or a hydroxyl radical, and
the symbol $R_4$ represents a hydrogen atom or, together with $R_3$, represents a fluorine atom, are of particular interest.

And among these products, the following products are more particularly advantageous:

2-{{[3-(1-pyrrolidinyl)-2-propoxy]phenyl}acetyl}-4,4-diphenyl-7-fluoroperhydroisoindole, 4,4-diphenyl-7-fluoro-2-[(S)-2-(2-methoxyphenyl)-propionyl]perhydroisoindole, 2-{[2-(3-dimethylaminopropoxy)phenyl]acetyl}-4,4-diphenyl-7-fluoroperhydroisoindole, 7,7-diphenyl-2-[(S)-2-(2-methoxyphenyl)propionyl]-4-perhydroisoindolol, 2-[(2-methoxyphenyl)acetyl]-4,4-diphenyl-7-fluoroperhydroisoindole, in their stereoisomeric forms as well as mixtures thereof and, where appropriate, their salts.

EXAMPLES

The following examples, which are given with no limitation being implied, illustrate the present invention.

In the examples below, it is understood, unless specifically stated, that the proton NMR spectra were established at 250 MHz in dimethyl sulphoxide; the chemical shifts are expressed in ppm.

EXAMPLE 1

A solution of 0.5 g of 1-(3-dimethylaminopropyl)-3-ethylcarbodiimide in 50 cm$^3$ of dry dichloromethane is added over 10 minutes to a solution, cooled to +4° C., of 0.72 g of (3aR,7R,7aR)-4,4-diphenyl-7-fluoroperhydroisoindole, 0.5 g of 2-(3-dimethylaminopropoxy)-phenylacetic acid, 0.03 g of 1-hydroxybenzotriazole in 75 cm$^3$ of dichloromethane, followed by 0.37 cm$^3$ of diisopropylethylamine. The reaction mixture is stirred for 3 hours at 0° C. and then washed twice with 50 cm$^3$ of water and twice with 50 cm$^3$ of a saturated solution of sodium chloride. The organic phase is dried over magnesium sulphate and concentrated to dryness under reduced pressure (2.7 kPa). The residue is taken up in 21 cm$^3$ of 0.1N hydrochloric acid, 50 cm$^3$ of diethyl ether and 30 cm$^3$ of water. The aqueous phase is separated and freeze-dried to give 0.85 g of (3aR,7R,7aR)-2-{[2-(3-dimethylaminopropoxy)phenyl]acetyl}-4,4-diphenyl-7-fluoroperhydroisoindole hydrochloride, in the form of a white freeze-dried product.

Infrared spectrum (KBr, characteristic bands, cm$^{-1}$): 3060, 3030, 2960, 2890, 2800, 2200, 1635, 1605, 1495, 1460, 1445, 1250, 755, 705.

Proton NMR spectrum (DMSO-d$_6$) (at room temperature, a mixture of the two rotamers is observed): 0.95–1.35 and 1.8–2.1 (2mt, 2×1H, CH$_2$ in 6); 2.6–2.8 (mt, 6H, N(CH$_3$)$_2$); 3.9 and 4.05 (2mt, 2×1H, OCH$_2$); 4.8 and 4.85 (broad 2d, J=50, 1H, CHF); 6.8 to 7.5 (mt, 14H, aromatics).

(3aR,7R,7aR)-4,4-Diphenyl-7-fluoroperhydroisoindole hydrochloride may be obtained in the following manner:

A solution of 2.25 g of (3aR,7R,7aR)-2-t-butoxycarbonyl-4,4-diphenyl-7-fluoroperhydroisoindole in 25 cm$^3$ of dioxane is treated with a 5.8N solution of hydrochloric acid in dioxane and stirred for 2 hours at 20° C. and then concentrated to dryness under reduced pressure (2.7 kPa). The residue is concentrated by adding 100 cm$^3$ of isopropyl oxide, the solid is filtered and dried to give 1.8 g of (3aR,7R,7aR)-4,4-diphenyl-7-fluoroperhydroisoindole hydrochloride, in the form of a cream-colored powder. Proton NMR spectrum (DMSO-d$_6$): 1.0–1.35 (mt, 1H of CH$_2$ in 6); 4.9 (broad d, J=50, 1H, CHF); 7.1 to 7.5 (mt, 14H, aromatics); 9.05 and 9.9 (2 mf, 2×1H, NH$_2$+).

(3aR,7R,7aR)-2-t-Butoxycarbonyl-4,4-diphenyl-7-fluoroperhydroisoindole may be obtained in the following manner:

A solution of 4.87 g of (3aR,7S,7aR)-2-t-butoxy-carbonyl-4,4-diphenyl-7-trifluoromethylsulphonyloxy-perhydroisoindole in 150 cm$^3$ of dry dichloromethane is treated with 22.6 cm$^3$ of a 1M solution of tetrabutylammonium fluoride in tetrahydrofuran and then stirred for 17 hours at 20° C. and concentrated to dryness under reduced pressure (2.7 kPa). The residue is chromatographed on a silica gel column (particle size 0.2–0.063 mm, diameter 4.5 cm, height 35 cm), eluting under a nitrogen pressure of 0.4 bar with a cyclohexane and ethyl acetate mixture (75/25) and collecting fractions of 20 cm$^3$. Fractions 28 to 38 are pooled and concentrated to dryness under reduced pressure (2.7 kPa) to give 1.44 g of (3aR,7R,7aR)-2-t-butoxycarbonyl-4,4-diphenyl-7-fluoro-perhydroisoindole, in the form of white crystals; melting point 200° C., $[\alpha]_D^{20}=-225°$ (c=1, CHCl$_3$).

(3aR,7S,7aR)-2-t-Butoxycarbonyl-4,4-diphenyl-7-trifluoromethylsulphonyloxyperhydroisoindole may be obtained in the following manner:

1.5 cm$^3$ of pyridine are added to a solution, cooled to −30° C., of 6.7 g of (3aR,4S,7aR)-2-t-butoxycarbonyl-7,7-diphenyl-4-perhydroisoindolol in 100 cm$^3$ of dry dichloromethane, followed, over 10 minutes, with a solution of 3.2 g of trifluoromethanesulphonic anhydride in 25 cm$^3$ of dry dichloromethane. The reaction mixture is stirred for 2 hours at −30° C. and then diluted with 250 cm$^3$ of water and 100 cm$^3$ of dichloromethane. The organic phase is washed with 200 cm$^3$ of a saturated solution of sodium bicarbonate and with 200 cm$^3$ of a saturated solution of sodium chloride and then dried and concentrated to dryness under reduced pressure (2.7 kPa) to give 8.6 g of (3aR,7S,7aR)-2-t-butoxycarbonyl-4,4-diphenyl-7-trifluoromethylsulphonyloxyperhydroisoindole, in the form of a yellow meringue which is used as it is in subsequent stages of the synthesis.

(3aR,4S,7aR)-2-t-Butoxycarbonyl-7,7-diphenyl-4-perhydroisoindolol may be obtained in the following manner:

10.55 g of di-tert-butyl dicarbonate are added to a solution of 13 g of (3aR,4S,7aR)-7,7-diphenyl-4-perhydroiso-indolol and 0.5 g of 4-dimethylaminopyridine in 450 cm$^3$ of dichloromethane. After stirring for 2 hours at 25° C., the reaction mixture is concentrated to dryness under reduced pressure (2.7 kPa) and the residue is crystallized from 50 cm$^3$ of ethyl ether. 9 g of (3aR,4S,7aR)-2-t-butoxycarbonyl-7,7-diphenyl-4-perhydroisoindolol are obtained in the form of white crystals; melting point 190° C.

(3aR,4S,7aR)-7,7-Diphenyl-4-perhydroisoindolol may be obtained in the following manner:

7.18 g of a solution of sodium borohydride in 500 cm$^3$ of methanol supplemented with 20 drops of a concentrated solution of sodium hydroxide (20 drops) is added over 90 minutes to a solution, cooled to 5° C., of 100 g of (3aR,7aR)-7,7-diphenyl-4-perhydroisoindolone hydrochloride in 1000 cm$^3$ of absolute methanol. After stirring for 2.5 hours between 5 and 10° C., the crystals formed are drained and taken up in 900 cm$^3$ of water and 1000 cm$^3$ of ethyl ether. The solution is filtered and alkalised with 15 cm$^3$ of a 4N solution of sodium hydroxide and then stirred for 2 h at 5° C. The crystals formed are drained, washed with ethyl ether and dried to give 28.8 g of (3aR,7S,7aR)-7,7-diphenyl-4-perhydroisoindolol in the form of white crystals; melting point 205° C., $[\alpha]_D^{20}=-230°$ (c=1, CHCl$_3$).

(3aR,7aR)-7,7-Diphenyl-4-perhydroisoindolone hydrochloride may be prepared in the following manner:

500 cm$^3$ of a 4N aqueous sodium hydroxide are slowly added, with stirring, to a suspension of 200 g of (3aRS,7aRS)-7,7-diphenyl-4-perhydroisoindolone hydrochloride in 2000 cm$^3$ of ethyl acetate; the stirring is continued until dissolution of the starting product. The organic solution is washed with 250 cm$^3$ of distilled water, with 250 cm$^a$ of a saturated aqueous solution of sodium chloride, dried over magnesium sulphate and filtered. A solution of 92.8 g of L(+)-mandelic acid in 1000 cm$^3$ of ethyl acetate is added, with stirring, to the solution thus obtained; after stirring for 4 hours, the crystals obtained are drained, washed with 250 cm$^3$ of ethyl acetate (twice) and dried. The crystals are taken up in 2000 cm$^3$ of distilled water; the mixture is refluxed, with stirring, for 15 minutes; the insoluble crystals are drained, washed with 100 cm$^3$ of distilled water (twice) and dried. They are recrystallized from a mixture of 1100 cm$^3$ of acetonitrile and 500 cm$^3$ of distilled water; the crystals obtained are drained, washed with 40 cm$^3$ of acetonitrile (3 times) and dried. 80 g of (3aR,7aR)-7,7-diphenyl-4-perhydroisoindolone (L)-mandelate are obtained; $[\alpha]_D^{20}=-164°$ (c=1, methanol).

400 cm$^3$ of 1N aqueous sodium hydroxide and 600 cm$^3$ of ethyl acetate are added to 80 g of (3aR,7aR)-7,7-diphenyl-4-perhydroisoindolone (L)-mandelate; the mixture is stirred at room temperature until dissolution of the starting product; the organic solution is washed with 250 cm$^3$ of distilled water, with 250 cm$^3$ of a saturated aqueous solution of sodium chloride, dried over magnesium sulphate and filtered; it is acidified, with stirring, by adding 30 cm$^3$ of 9N hydrochloric acid; the crystals obtained are drained, washed with 50 cm$^3$ of ethyl acetate (twice), with 50 cm$^3$ of isopropyl oxide and dried. 52.3 g of (3aR,7aR)-7,7-diphenyl-4-perhydroisoindolone hydrochloride are obtained; melting point 270° C., with decomposition; $[\alpha]_D^{20}=-282°$ (c=0.5, methanol).

(3aRS,7aRS)-7,7-Diphenyl-4-perhydroisoindolone hydrochloride may be prepared according to the following method:

150 g of (3aRS,7aRS)-2-benzyl-7,7-diphenyl-4-perhydroisoindolone, 1500 cm$^3$ of methanol and 450 cm$^3$ of 1N hydrochloric acid are added to 15 g of 10% palladium on charcoal; the reaction mixture is hydrogenated, with stirring, at room temperature and at atmospheric pressure. The theoretical volume of hydrogen was absorbed after 5 hours of reaction; the reaction mixture is filtered and then concentrated to dryness under reduced pressure (2.7 kPa); the residue is crystallized from 200 cm$^3$ of ethanol; the crystals obtained are drained, washed with 50 cm$^3$ of ethanol and dried. 110 g of (3aRS,7aRS)-7,7-diphenyl-4-perhydroisoindolone hydrochloride are obtained; melting point 270° C., with decomposition.

Proton NMR spectrum: 2.03 (Mt, 1H, 1H of H in 5 or 6); 2.3 (Mt, 1H, 1H of —H in 5 or 6); 2.48 (DD, partially masked, 1H of —CH$_2$— in 1); 2.69 (DD, 1H, 1H of —CH$_2$— in 1); 2.8 (Mt, 2H, —CH$_2$— in 6 or 5); 3.34 (DD, partially masked, 1H of —CH$_2$— in 3); 3.5 (Mt, 1H, —CH— in 3a); 3.82 (DD, 1H, 1H of —CH$_2$— in 3); 3.95 (Mt, 1H, —CH— in 7a); 7.15 to 7.65 (Mt, 10H, aromatics); 9.43 (Mf, 2H, —NH$_2$—Cl). Infrared spectrum (KBr) characteristic bands in cm$^{-1}$: 3600—3300, 3100—3000, 3000—2850, 3100—2400, 1715, 1595, 1580, 1495, 1470, 1445, 775, 750, 705.

(3aRS,7aRS)-2-Benzyl-7,7-diphenyl-4-perhydroisoindolone may be prepared in the following manner:

5 drops of trifluoroacetic acid are added to a solution of 155 g of 4,4-diphenyl-2-cyclohexen-1-one and 202 cm$^3$ of N-butoxymethyl-N-trimethylsilylmethylbenzylamine in 1000 cm$^3$ of dry dichloromethane and the reaction mixture is refluxed for 45 minutes. 50 cm$^3$ of N-butoxy-methyl-N-trimethylsilylmethylbenzylamine and 3 drops of trifluoroacetic acid are added and the mixture is further stirred for 45 minutes under reflux before again adding 25 cm$^3$ of N-butoxymethyl-N-trimethylsilyl-methylbenzylamine and 3 drops of trifluoroacetic acid. The reaction mixture is stirred under reflux for 45 minutes and then treated with 50 g of potassium carbonate, filtered and concentrated to dryness under reduced pressure (2.7 kPa). The residue is dissolved in 200 cm$^3$ of isopropyl oxide and the solution is cooled at 0° C. for 1 hour. The crystals are drained, washed twice with 15 cm$^3$ of isopropyl oxide and dried to give 193 g of (3aRS,7aRS)-2-benzyl-7,7-diphenyl-4-perhydroisoindolone in the form of white crystals; melting point 132° C.

N-Butoxymethyl-N-trimethylsilylmethylbenzylamine may be prepared according to the method of Y. Terao et al., Chem. Pharm. Bull., 33, 2762 (1985).

EXAMPLE 2

0.04 g of hydroxybenzotriazole hydrate is added to a solution, cooled to +5° C., of 1 g of (3aR,7R,7aR)-4,4-diphenyl-7-fluoroperhydroisoindole hydrochloride and 0,924 g of 2-{[3-(1-pyrrolidinyl)-2-propoxy]phenyl}acetic acid in 40 cm$^3$ of dry dichloromethane followed by 0.79 g of 1-(3-dimethylaminopropyl)-3-ethylcarbodiimide hydrochloride and 0.51 cm$^3$ of diisopropylethylamine. After stirring for 2.5 hours at +5° C. and 20 hours at 20° C., the reaction mixture is washed twice with 50 cm$^3$ of water, dried over magnesium sulphate and then concentrated to dryness at 40° C. under reduced pressure (2.7 kPa). The residue is chromatographed on a silica gel column (particle size 0.04–0.06 mm, diameter 2.4 cm, height 31 cm), eluting under a nitrogen pressure of 0.5 bar with an ethyl acetate, acetic acid and water mixture (60/10/10 by volume) and collecting fractions of 25 cm$^3$. Fractions 11 to 31 are pooled and concentrated to dryness under reduced pressure (2.7 kPa). The residue is taken up in 20 cm$^3$ of dichloromethane, the solution is washed with 20 cm$^3$ of a 1N aqueous solution of sodium hydroxide and then dried over magnesium sulphate and concentrated to dryness. This wash with a basic solution is repeated again. 0.68 g of (3aR,7R,7aR)-2-{{[3-(1-pyrrolidinyl)-2-propoxy]phenyl}acetyl}-4,4-diphenyl-7-fluoroperhydro-isoindole is obtained in the form of a white solid.

Infrared spectrum (KBr, characteristic bands, cm$^{-1}$): 3085, 3055, 3035, 2950, 2875, 2785, 1640, 1600, 1495, 1455, 1440, 1245, 750, 700. Proton NMR spectrum (DMSO-d$_6$+CF$_3$COOD): 1.1–1.45 (mt, 1H, 1H in 6); 1.9 (mt, 4H, 2CH$_2$ in 3 and 4 of pyrrolidino); 2.27 (mt, 1H, 1H in 5); 3.77 (d, J=10, 1H, H in 1); 4.03 (mt, 2H, OCH$_2$); 4.78 (broad d, J=50, 1H, CHF); 7.1 to 7.5 (mt, 14H, aromatics).

The hydrochloride salt of {[3-(1-pyrrolidinyl)-2-propoxy]phenyl}acetic acid may be prepared in the following manner:

700 cm$^3$ of a 6N solution of hydrochloric acid are added to 24.9 g of methyl {[3-(1-pyrrolidinyl)-2-propoxy]-phenyl}acetate. After refluxing for 2 hours, the solution is concentrated to dryness at 50° C. under reduced pressure. The residue is then taken up in 100 cm$^3$ of toluene and the solution is then concentrated to dryness under reduced pressure. After an identical treatment with toluene, 21.9 g of the hydrochloride salt of {[3-(1-pyrrolidinyl)-2-propoxy]phenyl}acetic acid are obtained in the form of a beige solid; melting point 173° C.

Proton NMR spectrum (250 MHz, DMSO-d$_6$): 1.8 to 2.1 (mt, 4H, —N(CH$_2$CH$_2$)$_2$); 2.15 (mt, 2H, CH$_2$—CH$_2$—CH$_2$); 2.98 and 3.52 (2mt, 2×2H, —N(CH$_2$CH$_2$)$_2$); 3.26 (mt, 2H, CH$_2$—N<); 3.5 (2s, 2H, CH$_2$COO); 4.06 (t, J=6, 2H, OCH$_2$); 6.32 (mt, 2H, aromatics in 3 and 5); 7.23 (mt, 2H, aromatics in 4 and 6); 11.2 (mf, 1H, —NH+<).

Methyl {[3-(1-pyrrolidinyl)-2-propoxy]-phenyl}acetate may be prepared in the following manner:

18.4 g of potassium carbonate, 4.5 g of sodium iodide and then 9.54 g of pyrrolidine are successively added to a solution of 36 g of methyl 2-(3-bromopropoxy)phenylacetate in 400 cm$^3$ of acetonitrile. The reaction mixture is refluxed for 5 hours and then stirred at 20° C. for 20 hours and diluted with 800 cm$^3$ of dichloromethane. The solution is washed with 80 cm$^3$ of water and then twice with 80 cm$^3$ of brine. The chloromethylenic phase is dried over sodium sulphate and concentrated to dryness under reduced pressure. The residue is chromatographed on a silica gel column (particle size 0.04–0.06 mm, diameter 4.5 cm, height 48 cm), eluting under a nitrogen pressure of 0.4 bar with an ethyl acetate and methanol mixture (90/10 by volume) and collecting fractions of 500 cm$^3$. Fractions 3 to 8 are pooled and concentrated to dryness at 50° C. under reduced pressure (2.7 kPa). 24.9 g of methyl {[3-(1-pyrrolidinyl)-2-propoxy]phenyl}acetate are obtained in the form of an orange-colored oil.

Infrared spectrum (CCl$_4$, characteristic bands, cm$^{-1}$): 3065, 3030, 2950, 2930, 2880, 2790, 1740, 1600, 1585, 1490, 1770, 1455, 1430, 1250.

Methyl 2-(3-bromopropoxy)phenylacetate may be prepared in the following manner:

254.5 g of potassium carbonate and 654 cm³ of 1,3-dibromopropane are added to a solution of 153 g of methyl (2-hydroxyphenyl)acetate in 1400 cm³ of acetonitrile. The suspension obtained is refluxed for 20 hours, cooled to 20° C. and then filtered The filtrate is concentrated to dryness at 50° C. under reduced pressure. The residue is chromatographed on a silica gel column (particle size 0.04–0.06 mm, diameter 8.8 cm, height 43 cm), eluting under a nitrogen pressure of 0.5 bar with a cyclohexane and ethyl acetate mixture (95/5 by volume) and collecting fractions of 300 cm³. Fractions 18 to 53 are pooled and concentrated to dryness under reduced pressure (2.7 kPa). 130.6 g of methyl 2-(3-bromopropoxy)phenylacetate are obtained in the form of an orange-coloured oil.

Proton NMR spectrum (250 MHz, CDCl₃): 2.32 (qt, J=6.5, 2H, CH₂—CH₂—CH₂); 3.26 (t, J=6.5, 2H, CH₂Br); 3.65 (s, 2H, COOCH₃); 3.7 (s, 2H, CH₂COO); 4.13 (t, J=6.5, 2H, OCH₂); 6.94 (mt, 2H, aromatics in 3 and 5); 7.25 (mt, 2H, aromatics in 4 and 6).

EXAMPLE 3

By carrying out the procedure as in Example 9 below, using 0.16 g of 2-dimethylaminophenylacetic acid and 0.30 g of (3aR,7S,7aR)-4,4-diphenyl-7-fluoroperhydroisoindole hydrochloride, 0.11 g of (3aR,7S,7aR)-2-[(2-dimethyl-aminophenyl)acetyl]-4,4-diphenyl-7-fluoroperhydroiso-indole is obtained in the form of a white meringue.

Infrared spectrum (KBr, characteristic bands, cm⁻¹) 3090, 3060, 3030, 2940, 2875, 2825, 2770, 1645, 1595, 1580, 1495, 1450, 1420, 755, 730, 700. Proton NMR spectrum (at room temperature, a mixture of the two rotamers is observed): 2.35 and 2.58 (2s, 6H, N(CH₃)2), 4.2–4.6 (mt, 1H, CHF), 6.9–7.5 (mt, 14H, aromatics).

(3aR,7S,7aR)-4,4-Diphenyl-7-fluoroperhydroisoindole hydrochloride may be prepared in the following manner:

By carrying out the procedure as in Example 8 below, using 0.5 g of (3aR,7S,7aR)-2-tert-butyloxy-carbonyl-4,4-diphenyl-7-fluoroperhydroisoindole, 0.35 g of (3aR,7S,7aR)-4,4-diphenyl-7-fluoroperhydroisoindole hydrochloride is obtained in the form of a grey solid. Infrared spectrum (KBr, characteristic bands, cm⁻¹): 3420, 3090, 3050, 3025, 2970, 2920, 2800–2250, 1590, 1580, 1495, 1460, 1445, 1060, 750, 730, 700.

(3aR,7S,7aR)-2-tert-Butyloxycarbonyl-4,4-diphenyl-7-fluoroperhydroisoindole may be prepared in the following manner:

A solution of 0.37 cm³ of 4-trifluorothiomorpholine in 10 cm³ of dry dichloromethane is added to a solution, cooled to +5° C., of 1.0 g of (3aR,4R,7aR)-2-tert-butyloxycarbonyl-7,7-diphenyl-4-perhydroisoindolol in 20 cm³ of dry dichloromethane. After stirring for 2 hours at +5° C., the reaction mixture is washed with 20 cm³ of a 5% aqueous solution of sodium bicarbonate and then dried over magnesium sulphate and concentrated to dryness under reduced pressure (2.7 kPa). The residue is chromatographed on a silica gel column (particle size 0.04 mm–0.06 mm, diameter 2.4 cm, height 35 cm), eluting under a nitrogen pressure of 0.8 bar with a cyclohexane and ethyl acetate mixture (90/10 by volume) and collecting fractions of 25 cm³. Fractions 25 to 34 are pooled and concentrated to dryness. 0.27 g of (3aR,7S,7aR)-2-tert-butyloxycarbonyl-4,4-diphenyl-7-fluoroperhydroiso-indole is obtained in the form of a white meringue.

Infrared spectrum (KBr, characteristic bands, cm⁻¹): 3090, 3060, 3030, 2975, 2930, 2875, 1695, 1595, 1580, 1495, 1450, 1405, 1365, 1175, 755, 730, 700.

EXAMPLE 4

0.28 cm³ of triethylamine and 0.32 g of carbonyldiimidazole are added to a solution, cooled to 4° C., of 0.57 g of the hydrobromide salt of (2-pyrrolidinophenyl)acetic acid in 20 cm³ of dry dichloromethane. The mixture is stirred for one hour at +4° C. and then a solution of 0.67 g of (3aR,7R,7aR)-4,4-diphenyl-7-fluoroperhydroisoindole hydrochloride in 20 cm³ of dry dichloromethane and 0.28 cm³ of triethylamine, is added. The reaction mixture is stirred at room temperature for 24 hours and then diluted with 100 cm³ of dichloromethane, washed twice with 50 cm³ of water, dried over magnesium sulphate, filtered and concentrated to dryness under reduced pressure (2.7 kPa). The residue is chromatographed on a silica gel column (particle size 0.04–0.06 mm, diameter 3.5 cm, height 38 cm), eluting under a nitrogen pressure of 0.5 bar with a cyclohexane and ethyl acetate mixture (70/30 by volume) and collecting fractions of 20 cm³. Fractions 26 to 54 are pooled and concentrated to dryness under reduced pressure (2.7 kPa). The residue is crystallized from an acetonitrile and diisopropyl oxide mixture (25/75 by volume). 0.16 g of (3aR,7R,7aR)-4,4-diphenyl-7-fluoro-2-[(2-pyrrolidinophenyl)acetyl]perhydroisoindole is obtained in the form of white crystals; melting point 170° C.

EXAMPLE 5

0.17 g of carbonyldiimidazole is added to a solution, cooled to +4° C., of 0.19 g of (2-dimethylaminophenyl)-acetic acid in 15 cm³ of dry dichloromethane. The mixture is stirred for one hour at +4° C. and then a solution of 0.35 g (3aR,7R,7aR)-7-chloro-4,4-diphenylperhydro-isoindole hydrochloride in 10 cm³ of dry dichloromethane is then added followed by a solution of 0.15 cm³ of triethylamine in 10 cm³ of dry dichloromethane. The reaction mixture is stirred at room temperature for 20 hours and then diluted with 120 cm³ of dichloromethane, washed with 80 cm³ of water and then with a saturated aqueous solution of sodium chloride, dried over magnesium sulphate, filtered and concentrated to dryness under reduced pressure (2.7 kPa). The residue is chromatographed on a silica gel column (particle size 0.04–0.06 mm, diameter 2 cm, height 22 cm), eluting under a nitrogen pressure of 0.4 bar with an ethyl acetate and cyclohexane mixture (75/25 by volume) and collecting fractions of 20 cm³. Fractions 6 to 9 are pooled and concentrated to dryness under reduced pressure (2.7 kPa). The product, which is obtained in the form of a base, is converted to the hydrochloride by dissolving in 25 cm³ of ethyl ether, followed by the addition of 5 cm³ of a 3.2N solution of hydrochloric acid to the ethyl ether, washing with ethyl ether and drying. 0.14 g of (3aR,7R,7aR)-7-chloro-2-[(2-dimethylamino-phenyl)acetyl]-4,4-diphenylperhydroisoindole hydrochloride is obtained in the form of white crystals; melting point 190° C.

(3aR,7R,7aR)-7-Chloro-4,4-diphenylperhydroisoindole hydrochloride may be obtained in the following manner:

A solution of 0.4 g of (3aR,7R,7aR)-7-chloro-2-chlorocarbonyl-4,4-diphenylperhydroisoindole in 6 cm³ of a 1N aqueous solution of hydrochloric acid and 14 cm³ of tetrahydrofuran is heated at 80° C. for 9 hours, with stirring. The reaction mixture is concentrated to dryness under reduced pressure (2.7 kPa). 0.35 g of (3aR,7R,7aR)-7-chloro-4,4-diphenylperhydroisoindole hydrochloride is obtained in the form of a white solid.

Infrared spectrum (KBr, characteristic bands, cm$^{-1}$): 3055, 3025, 3000, 2250, 1600, 1495, 1580, 1460, 1445, 1435, 760, 750, 735, 700.

(3aR,7R,7aR)-7-Chloro-2-chlorocarbonyl-4,4-diphenylperhydroisoindole may be obtained in the following manner:

1.3 g of calcium carbonate and then 2 g of phosphorus pentachloride are successively added to a solution, cooled to +4° C., of 1 g of (3aR,4S,7aR)-7,7-diphenyl-2-tert-butyloxycarbonyl-4-perhydroisoindolol in 60 cm$^3$ of chloroform, and the mixture is stirred at room temperature for 20 hours. The reaction mixture is then filtered, diluted with 80 cm$^3$ of chloroform, washed twice with 80 cm$^3$ of water, dried over magnesium sulphate and concentrated to dryness under reduced pressure (2.7 kPa). The residue is chromatographed on a silica gel column (particle size 0.04–0.06 mm, diameter 2.5 cm, height 34 cm), eluting under a nitrogen pressure of 0.4 bar with a cyclohexane and ethyl acetate mixture (30/70 by volume) and collecting fractions of 20 cm$^3$. Fractions 7 to 10 are pooled and concentrated to dryness under reduced pressure (2.7 kPa). 0.44 g of (3aR,7R,7aR)-7-chloro-2-chlorocarbonyl-4,4-diphenylperhydroisoindole is obtained in the form of a white solid.

Infrared spectrum (CCl$_4$ solution, characteristic bands, cm$^{-1}$): 3090, 3065, 3035, 2930, 2855, 1745, 1600, 1585, 1495, 1450, 700.

EXAMPLE 6

0.39 g of carbonyldiimidazole is added to a solution, cooled to +4° C., of 0.43 g of (2-dimethylamino-phenyl)-acetic acid in 15 cm$^3$ of dry dichloromethane. The mixture is stirred for one hour at +4° C. and then a solution of 0.84 g of (3aR,7S,7aR)-7-chloro-4,4-diphenylperhydro-isoindole hydrochloride in 10 cm$^3$ of dry dichloromethane is then added followed by a solution of 0.34 cm$^3$ of triethylamine in 10 cm$^3$ of dry dichloromethane. The reaction mixture is stirred at room temperature for 20 hours and then diluted with 100 cm$^3$ of dichloromethane, washed with 50 cm$^3$ of water and then with a saturated aqueous solution of sodium chloride, dried over magnesium sulphate, filtered and concentrated to dryness under reduced pressure (2.7 kPa). The residue is chromatographed on a silica gel column (particle size 0.04–0.06 mm, diameter 3 cm, height 23 cm), eluting under a nitrogen pressure of 0.4 bar with an ethyl acetate and cyclohexane mixture (25/75 by volume) and collecting fractions of 80 cm$^3$. Fraction 2 is concentrated to dryness under reduced pressure (2.7 kPa). The product, which is obtained in the form of a base, is converted to the hydrochloride by dissolving in 4 cm$^3$ of acetonitrile followed by the addition of 6 cm$^3$ of a 3.2N solution of hydrochloric acid in ethyl ether, washing with isopropyl ether and drying. 0.08 g of (3aR,7S,7aR)-7-chloro-2-[(2-dimethylamino-phenyl)acetyl]-4,4-diphenylperhydroisoindole hydrochloride is obtained in the form of a beige solid.

Infrared spectrum (KBr, characteristic bands, cm$^{-1}$): 3055, 3025, 2950, 1635, 1490, 1460, 1440, 760, 750, 700. Proton NMR spectrum (DMSO-d$_6$) (at 403° K., a mixture of the two rotamers is observed, DMSO-d$_6$+CF$_3$COOD, main signals): 3 and 3.13 (2s, 6H, N(CH$_3$)2); 4.54 and 4.63 (2mt, 1H, CHCl); 7 to 7.8 (mt, 14H, aromatics).

(3aR,7S,7aR)-7-Chloro-4,4-diphenylperhydroisoindole hydrochloride may be obtained in the following manner:

10 cm$^3$ of a 6.3N solution of hydrochloric acid in dioxane are added to a solution of 1.03 g of (3aR,7S,7aR)-2-tert-butyloxycarbonyl-7-chloro-4,4-diphenyl-perhydroisoindole in 5 cm$^3$ of dioxane. The reaction mixture is stirred at room temperature for 2 hours and then concentrated to dryness under reduced pressure (2.7 kPa). 0.84 g of (3aR,7S,7aR)-7-chloro-4,4-diphenyl-perhydroisoindole hydrochloride is obtained in the form of a solid which is used in the crude state in the next test.

(3aR,7S,7aR)-2-tert-Butyloxycarbonyl-7-chloro-4,4-diphenylperhydroisoindole may be obtained in the following manner:

A solution of 1 g of (3aR,4S,7aR)-2-tert-butyloxycarbonyl-7,7-diphenyl-4-perhydroisoindolol in 10 cm$^3$ of thionyl chloride is stirred for 3 hours at 80° C. The reaction mixture is then concentrated to dryness under reduced pressure (2.7 kPa). 1.03 g of (3aR,7S,7aR)-2-tert-butyloxycarbonyl-7-chloro-4,4-diphenylperhydroisoindole are obtained in the form of a solid which is used in the crude state in the next test.

EXAMPLE 7

0.32 g of carbonyldiimidazole is added to a solution, cooled to +4° C., of 0.36 g of (S)-2-(2-methoxyphenyl)-propionic acid in 20 cm$^3$ of dry dichloromethane. The mixture is stirred for one hour at +4° C. and then a solution of 0.67 g of (3aR,7R,7aR)-4,4-diphenyl-7-fluoroperhydro-isoindole hydrochloride in 20 cm$^3$ of dry dichloromethane and 0.28 cm$^3$ of triethylamine, is added. The reaction mixture is stirred at room temperature for 20 hours, diluted with 200 cm$^3$ of dichloromethane and then washed with 50 cm$^3$ of water, dried over magnesium sulphate, filtered and concentrated to dryness under reduced pressure (2.7 kPa). The residue is chromatographed on a silica gel column (particle size 0.04–0.06 mm, diameter 3 cm, height 20 cm), eluting under a nitrogen pressure of 0.4 bar with an ethyl acetate and cyclohexane mixture (60/40 by volume) and collecting fractions of 20 cm$^3$. Fractions 10 to 15 are pooled and concentrated to dryness under reduced pressure (2.7 kPa). The residue is crystallized from 0.6 cm$^3$ of isopropyl oxide. The crystals obtained are drained, washed with isopropyl oxide and then dried. 0.19 g of (3aR,7R,7aR)-4,4-diphenyl-7-fluoro-2-[(S)-2-(2-methoxyphenyl)propionyl]perhydroisoindole is obtained in the form of white crystals; melting point 195° C.

(3aR,7R,7aR)-4,4-Diphenyl-7-fluoroperhydroisoindole hydrochloride may be obtained in the following manner:

40 cm$^3$ of a 6.3N solution of hydrochloric dioxane are added to a solution of 3.7 g of (3aR,7R,7aR)-4,4-diphenyl-7-fluoro-2-tert-butyloxycarbonylperhydro-isoindole in 40 cm$^3$ of dioxane, and the mixture is stirred at room temperature for 2 hours. The reaction mixture is concentrated to dryness under reduced pressure (2.7 kPa), triturated in diisopropyl oxide, filtered and dried. 3.1 g of (3aR,7R,7aR)-4,4-diphenyl-7-fluoroperhydroisoindole hydrochloride are obtained in the form of white crystals; melting point 200° C., with decomposition.

(3aR,7R,7aR)-4,4-Diphenyl-7-fluoro-2-tert-butyloxycarbonylperhydroisoindole may be obtained in the following manner:

A solution of 3.5 cm³ of morpholinosulphur trifluoride in 50 cm³ of dichloromethane is added to a solution, cooled to +5° C., of 9.4 g of (3aR,4S,7aR)-7,7-diphenyl-2-tert-butyloxycarbonyl-4-perhydroisoindolol in 250 cm³ of dry dichloromethane. The reaction mixture is stirred for 4 hours at +5° C. and then diluted with 300 cm³ of dichloromethane, washed with 250 cm³ of an aqueous solution of sodium hydrogen carbonate, dried over magnesium sulphate, filtered and concentrated to dryness under reduced pressure (2.7 kPa). The residue is chromatographed on a silica gel column (particle size 0.04–0.06 mm, diameter 3.5 cm, height 42 cm), eluting under a nitrogen pressure of 0.5 bar with a cyclohexane and ethyl acetate mixture (90/10 by volume) and collecting fractions of 120 cm³. Fractions 13 to 17 are pooled and concentrated to dryness under reduced pressure (2.7 kPa). The residue is crystallized from cyclohexane. 2.55 g of (3aR,7R,7aR)-4,4-diphenyl-7-fluoro-2-tert-butyloxycarbonylperhydroisoindole are obtained in the form of white crystals; melting point 202° C.

(S)-2-(2-Methoxyphenyl)propionic acid may be obtained in the following manner:

(S)-2-(2-Methoxyphenyl)propionic acid may be prepared by analogy with the methods described by D. A. Evans et al., Tetrahedron, 44, 5525, (1988), according to the following procedure:

1.52 g of lithium hydroxide are added to a solution, cooled to +5° C., of 4.1 g of (4S,5S)-4-methyl-5-phenyl-3-[(S)-2-(2-methoxyphenyl)-propionyl]-2-oxazolidinone in 60 cm³ of tetrahydrofuran and 30 cm³ of water. The reaction mixture is stirred for 3 hours at this temperature and then, after re-equilibrating to room temperature, ethyl acetate is added, the mixture is decanted and the aqueous phase is acidified with a 1N aqueous solution of hydrochloric acid, extracted with ethyl acetate and the organic phase is dried over magnesium sulphate and concentrated to dryness under reduced pressure (2.7 kPa). The solid obtained is recrystallized from hexane, drained and dried. 0.4 g of (S)-2-(2-methoxyphenyl)-propionic acid is obtained in the form of white crystals; melting point 102° C. $[\alpha]_D^{20} = +84.6°$ (c=1; CHCl₃).

(4S,5S)-4-Methyl-5-phenyl-3-[(S)-2-(2-methoxyphenyl)propionyl]-oxazolidinone may be obtained in the following manner:

19.1 g of sodium 1,1,1,3,3,3-hexamethyldisilazanate are added to a solution, cooled to −50° C., of 10 g of (4S,5S)-4-methyl-5-phenyl-3-[(2-methoxyphenyl)acetyl]-2-oxazolidinone in 150 cm³ of tetrahydrofuran and the mixture is stirred for 45 minutes at this temperature and then 7.72 cm³ of methyl iodide are added. The reaction mixture is then stirred for 15 hours at room temperature and then diluted with ethyl acetate, washed with 50 cm³ of water and then with 50 cm³ of a saturated aqueous solution of sodium chloride, dried over magnesium sulphate and concentrated to dryness under reduced pressure (2.7 kPa). The residue obtained is crystallized from isopropyl oxide, drained and dried. 4.2 g of (4S,5S)-4-methyl-5-phenyl-3-[(S)-2-(2-methoxyphenyl)-propionyl]-2-oxazolidinone are obtained in the form of a white solid.

(4S,5S)-4-Methyl-5-phenyl-3-(2-methoxyphenylacetyl)-2-oxazolidinone may be obtained in the following manner:

9.38 g of 2-methoxyphenylacetic acid are added to a suspension of 1.89 g of sodium hydride (80% 25 dispersion in vaseline) in 200 cm³ of dry tetrahydrofuran, at room temperature. This suspension is cooled to −30° C., 7.77 cm³ of pivaloyl chloride are added and then a solution, cooled to −78° C., which is obtained by adding 35.27 cm³ of a 1.6M solution of butyllithium in hexane to a solution, cooled to −78° C., of 10 g of (4S,5S)-4-methyl-5-phenyl-2-oxazolidinone in 200 cm³ of dry tetrahydrofuran is finally added. The reaction mixture is stirred for 45 minutes at −30° C. and then after re-equilibrating to room temperature, 200 cm³ of a saturated aqueous solution of ammonium chloride are added followed by 500 cm³ of ethyl acetate; after decantation, the organic phase is washed twice with 100 cm³ of water and then twice with 100 cm³ of a saturated aqueous solution of sodium chloride; dried over magnesium sulphate and concentrated to dryness under reduced pressure (2.7 kPa). The residue is chromatographed on a silica gel column (particle size 0.04–0.06 mm, diameter 4.8 cm, height 36 cm), eluting under a nitrogen pressure of 0.6 bar with a cyclohexane and ethyl acetate mixture (85/15 followed by 80/20 by volume) and collecting fractions of 50 cm³. Fractions 14 to 31 are pooled and concentrated to dryness under reduced pressure (2.7 kPa). 13.6 g of (4S,5S)-4-methyl-5-phenyl-3-(2-methoxyphenylacetyl)-2-oxazolidinone are obtained in the form of a yellow oil.

EXAMPLE 8

By carrying out the procedure as in Example 9 below, using 0.77 g of 2-dimethylaminophenylacetic acid and 1.50 g of (3aRS,7aRS)-4,4-diphenyl-7,7-difluoroperhydroiso-indole hydrochloride, 1.29 g of (3aRS,7aRS)-2-[(2-dimethylaminophenyl)acetyl]-4,4-diphenyl-7,7-difluoro-perhydroisoindole are obtained in the form of a white solid; melting point 189° C.

(3aRS,7aRS)-4,4-Diphenyl-7,7-difluoroperhydroisoindole hydrochloride may be prepared in the following manner:

20 cm³ of dioxane and 20 cm³ of 6.3N hydrochloric acid are added to 1.8 g of (3aRS,7aRS)-2-tert-butyloxycarbonyl-4,4-diphenyl-7,7-difluoroperhydroisoindole. After stirring for 20 hours at room temperature, the white suspension obtained is concentrated to dryness at 40° C. under reduced pressure (2.7 kPa). The residue is washed with diisopropyl oxide, the solid obtained is drained and then dried. 1.51 g of (3aRS,7aRS)-4,4-diphenyl-7,7-difluoroperhydroisoindole hydrochloride are obtained in the form of a white solid.

Infrared spectrum (KBr, characteristic bands, cm⁻¹): 3090, 3050, 3025, 2965, 2935, 2900, 2800−2250, 1595, 1580, 1495, 1465, 1445, 760, 730, 700. Proton NMR spectrum (DMSO-d₆+CF₃COOD): 1.2–1.55 and 2.12 (2mt, 2×1H, C₂ in 6); 3–3.3 (mt, 1H, H in 7a); 3.58 (mt, 2H, CH₂ in 1); 3.76 (mt, 1H, H in 3a); 7.1 to 7.5 (mt, 10H, aromatics).

(3aRS,7aRS)-2-tert-Butyloxycarbonyl-4,4-diphenyl-7,7-difluoroperhydroisoindole may be prepared in the following manner:

A solution of 5.0 g of (3aRS,7aRS)-2-tert-butyloxycarbonyl-7,7-diphenyl-4-perhydroisoindolone in 30 cm³ of dry dichloromethane is added to a solution of 3.4 cm³ of diethylaminosulphur trifluoride in 20 cm³ of dry dichloromethane. After stirring for 5 hours under reflux, and 20 hours at 20° C., the reaction mixture is washed with 50 cm³ of a saturated aqueous solution of sodium bicarbonate and with 50 cm³ of water and then dried over magnesium sulphate and concentrated to dryness. The residue is chromatographed on a silica gel column (particle size 0.04–0.06 mm, diameter 2.8 cm, height 35 cm), eluting under a nitrogen pressure of 0.8 bar with a cyclohexane and ethyl acetate mixture (95/5 followed by 90/10 by volume) and collecting fractions of 25 cm³. Fractions 24 to 52 are pooled and concentrated to dryness under reduced pressure (2.7 kPa). The residue is crystallized from ethyl acetate and diisopropyl oxide, the crystals are drained and then dried. 1.80 g of (3aRS,7aRS)-2-tert-butyloxycarbonyl-4,4-diphenyl-7,7-difluoroperhydroisoindole are obtained in the form of white crystals; melting point 162° C.

EXAMPLE 9

0.49 g of N,N'-carbonyldiimidazole is added to a solution of 0.52 g of 2-dimethylaminophenylacetic acid in 20 cm³ of dry dichloromethane. The mixture is stirred for 30 minutes at +5° C. and then a solution of 0.93 g of (3aR,4S,7aR)-7,7-diphenyl-4-perhydroisoindolol hydrochloride and 0.84 cm³ of triethylamine in 10 cm³ of dichloromethane, is added. The reaction mixture is stirred for 2 hours at +5° C. and then washed with 10 cm³ of water, dried over magnesium sulphate, filtered and concentrated to dryness under reduced pressure (2.7 kPa). The residue obtained is chromatographed on a silica gel column (0.04 mm–0.06 mm, diameter 2 cm, height 35 cm), eluting with ethyl acetate and collecting fractions of 30 cm³. Fractions 8 to 27 are pooled, concentrated to dryness under reduced pressure (2.7 kPa). The residue is crystallised-from a mixture of 4 cm³ of acetonitrile and 20 cm³ of ethyl ether. The crystals are drained and dried under reduced pressure (2.7 kPa). 0.70 g of (3aR,4S,7aR)-2-[(2-dimethylaminophenyl)-acetyl]-7,7-diphenyl-4-perhydroisoindolol is obtained in the form of a white solid; melting point 160° C., $[\alpha]_D^{20} = -162°$ (c=0.5, methanol).

EXAMPLE 10

By carrying out the procedure as in Example 9, using 0.26 g of 2-dimethylaminophenylacetic acid and 0.50 g of (3aR,4R,7aR)-7,7-diphenyl-4-perhydroisoindolol hydrochloride, 0.21 g of (3aR,4R,7aR)-2-[(2-dimethylaminophenyl)acetyl]-7,7-diphenyl-4-perhydroisoindolol is obtained in the form of a white solid; melting point 204° C., $[\alpha]_D^{20} = -212°$ (c=0.5, methanol).

(3aR,4R,7aR)-7,7-Diphenyl-4-perhydroisoindolol hydrochloride may be prepared by hydrogenation of a suspension of 0.70 g of (3aR,4R,7aR)-2-benzyl-7,7-diphenyl-4-perhydroisoindolol in 30 cm³ of methanol and 2.0 cm³ of 1N hydrochloric acid, at atmospheric pressure for 20 hours at 20° C. in the presence of 0.12 g of 20% palladium hydroxide on carbon black. The reaction mixture is filtered and concentrated to dryness under reduced pressure (2.7 kPa), the oil obtained is concreted with ethyl ether. The suspension is filtered, and the solid drained and dried under reduced pressure (2.7 kPa). 0.52 g of (3aR,4R,7aR)-7,7-diphenyl-4-perhydroisoindolol hydrochloride is obtained in the form of a white solid; melting point 220° C. (with decomposition).

Infrared spectrum (characteristic bands, c⁻¹): 3400, 3090, 3050, 3025, 3000–2800, 1600, 1580, 1495, 1465, 985, 750, 700. Proton NMR spectrum (DMSO-d₆, main signals): 1.06 (broad t, J=14, 1H, H in 5); 1.66 (broad d, J=14, 1H, H in 5); 2.17 (broad d, J=14, 1H, CH₂ in 6); 3.8 (broad s, 1H, H in 4); 5.3 (mf, 1H, OH); 7.05 to 7.45 (mt, 10H, aromatics); 8.4 and 9.43 (mf, 2H, NH₂⁺).

(3aR,4R,7aR)-2-Benzyl-7,7-diphenyl-4-perhydroisoindolol may be prepared in the following manner:

4.0 cm³ of a 1M solution of lithium tri-sec-butylborohyride in tetrahydrofuran is added over 5 minutes to a solution, cooled to 0° C., of 1.3 g of (3aR,7aR)-2-benzyl-7,7-diphenyl-4-perhydroisoindolone in 6.0 cm³ of tetrahydrofuran. After stirring for 3 hours at 0° C., 0.5 cm³ of the 1M solution of borohydride is again added to the reaction mixture. After 1 hour at 0° C., followed by the addition of 50 cm³ of water and 50 cm³ of ethyl acetate, the organic phase is decanted, washed with 20 cm³ of water, dried over magnesium sulphate and concentrated to dryness under reduced pressure (2.7 kPa). The oil obtained is crystallized from 30 cm³ of diisopropyl oxide, the crystals are drained and dried under reduced pressure (2.7 kPa). 0.70 g of (3aR,4R,7aR)-2-benzyl-7,7-diphenyl-4-perhydroisoindolol is obtained in the form of white crystals; melting point 154° C.

(3aR,7aR)-2-Benzyl-7,7-diphenyl-4-perhydroisoindolone may be prepared in the following manner:

7.9 cm³ of benzyl bromide are added to a solution, cooled to 0° C., of 21.7 g of (3aR,7aR)-7,7-diphenyl-4-perhydroisoindolone hydrochloride in 300 cm³ of dichloromethane, and 18.5 cm³ triethylamine. After stirring for 1 hour at 0° C. and 2 hours at 20° C., the reaction mixture is washed with 50 cm³ of water, dried 15 over magnesium sulphate and concentrated to dryness under reduced pressure (2.7 kPa). The residue is chromatographed on a silica gel column (0.04–0.06 mm, diameter 5 cm, height 40 cm), eluting of 250 cm³ under a nitrogen pressure of 0.6 bar with an ethyl acetate and cyclohexane mixture (75/25 by volume) and collecting fractions of 250 cm³. Fractions 3 to 6 are pooled and concentrated to dryness under reduced pressure (2.7 kPa). 22.1 g (3aR,7aR)-7,7-benzyl-4-perhydroisoindolone are obtained in the form of a white solid; melting point 124° C. $[\alpha]_D^{20} = -279°$.

EXAMPLE 11

0.42 cm³ of triethylamine and 0.49 g of carbonyldiimidazole are added to a solution, cooled to +4° C., of 0.86 g of the hydrobromide salt of (2-pyrrolidinophenyl)acetic acid in 20 cm³ of dry dichloromethane. The mixture is stirred for one hour at 4° C. and then a solution of 1 g of (3aR,4S,7aR)-7,7-diphenyl-4-perhydroisoindolol hydrochloride and 0.42 cm³ of triethylamine in 10 cm³ of dry dichloromethane, is added. The reaction mixture is stirred at room temperature for 24 hours, and then washed twice with 10 cm³ of water and then with an aqueous solution of sodium hydrogen carbonate, dried over magnesium sulphate, filtered and concentrated to dryness under reduced pressure (2.7 kPa). The product, which is obtained in the form of a base, is converted to the hydrochloride by dissolving in the minimum amount of acetone, by treating with a solution of hydrochloric acid in ethyl ether, and by adding ethyl ether. The solid obtained is triturated in ethyl ether and then dried. 0.2 g of (3aR,4S,7aR)-7,7-diphenyl-2-[(2-pyrrolidinophenyl)acetyl]-4-perhydroisoindolol hydrochloride is obtained in the form of a beige solid.

Infrared spectrum (KBr, characteristic bands, cm⁻¹): 3085, 3050, 3025, 2945, 2880, 2750, 2250, 1640, 1600, 1495, 1445, 1060, 755, 730, 700. Proton NMR spectrum (DMSO-d₆): 0.92 and 1.72 (2 mt, 2×1H, CH₂— in 5); 2.17 (mt, 4H, 2 CH₂ in 3 and 4 of pyrrolidino); 7 to 7.8 (mt, 14H, aromatics).

EXAMPLE 12

By carrying out the procedure as described above in Example 9, using 1.82 g of (2-methoxyphenyl)acetic acid and 3.29 g of (3aR,4S,7aR)-7,7-diphenyl-4-perhydroisoindolol hydrochloride, 3.9 g of (3aR,4S,7aR)-2-[(2-methoxyphenyl)acetyl]-7,7-diphenyl-4-perhydroisoindolol are obtained in the form of a white solid; melting point 246° C. $[\alpha]_D^{20} = -174°$ (c=0.37; methanol)

EXAMPLE 13

0.37 g of carbonyldiimidazole is added to a solution, cooled to +4° C., of 0.41 g of (S)-2-(2-methoxyphenyl)-propionic acid in 15 cm$^3$ of dry dichloromethane. The mixture is stirred for one hour at 4° C. and then a solution of 0.75 g (3aR,4S,7aR)-7,7-diphenyl-4-perhydroisoindolol hydrochloride is added. The reaction mixture is stirred at room temperature for 20 hours and then then washed twice with 10 cm$^3$ of water, dried over magnesium sulphate, filtered and concentrated to dryness under reduced pressure (2.7 kPa). The residue is chromatographed on a silica gel column (particle size 0.04–0.06 mm, diameter 3.6 cm, height 37 cm), eluting under a nitrogen pressure of 0.5 bar with an ethyl acetate and cyclohexane mixture (50/50 by volume) and collecting fractions of 50 cm$^3$. Fractions 21 to 41 are pooled and concentrated to dryness under reduced pressure (2.7 kPa). The residue is triturated in isopropyl oxide and then dried. 0.3 g of (3aR,4S,7aR)-7,7-diphenyl-2-[(S)-2-(2-methoxyphenyl)propionyl]-4-perhydroisoindolol is obtained in the form of a white meringue.

Infrared spectrum (KBr, characteristic bands, cm$^{-1}$): 3090, 3060, 3030, 2940, 2875, 2840, 1630, 1600, 1495, 1445, 1245, 1060, 755, 730, 700. Proton NMR spectrum (DMSO-d$_6$) (at room temperature, a mixture of the two rotamers is observed): 0.9–1.8 (mt, 2H, CH$_2$ in 5); 1.14 and 1.23 (2d, J=7, 3H, CH$_3$); 3.55 mixture of the two rotamers is observed): 0.09–1.8 (mt, 2H, CH$_2$ in 5); 1.14 and 1.23 (2d, J=7, 3H, CH$_3$; 3.55 and 3.65 (2s, 3H, OCH$_3$); 3.85 and 4.23 (2mt, 1H, —COCHCH$_3$—); 6.8 to 7.5 (mt, 14H, aromatics).

(3aR,4S,7aR)-7,7-Diphenyl-4-perhydroisoindolol hydrochloride may be obtained in the following manner:

40 cm$^3$ of a 6.3N solution of hydrochloric dioxane are added to a solution of 2 g of (3aR,4S,7aR)-7,7-diphenyl-2-tert-butyloxycarbonyl-4-perhydroisoindolol in 20 cm$^3$ of dioxane, and the mixture is stirred at room temperature for 5 hours. The reaction mixture is concentrated to dryness under reduced pressure (2.7 kPa), triturated in acetonitrile, filtered and dried. 1.57 g of (3aR,4S,7aR)-7,7-diphenyl-4-perhydroisoindolol hydrochloride are obtained in the form of white crystals; melting point 266° C.

(3aR,4S,7aR)-7,7-Diphenyl-2-tert-butyloxycarbonyl-4-perhydroisoindolol and (3aR,4R,7aR)-7,7-diphenyl-2-tert-butyloxycarbonyl-4-perhydroisoindolol may be obtained in the following manner:

A solution of 1 g of sodium borohydride in 200 cm$^3$ of methanol is added dropwise over 40 minutes to a solution, cooled to +4° C. of 17.8 g of (3aR,7aR)-7,7-diphenyl-2-tert-butyloxycarbonyl-4-perhydroisoindolone in one liter of methanol, followed by 10 drops of caustic soda. The reaction mixture is stirred for 3 hours at +4° C. and then 2 cm$^3$ of a 0.1N aqueous solution of hydrochloric acid are added and the mixture is concentrated to dryness under reduced pressure (2.7 kPa). The residue is dissolved in 350 cm$^3$ of dichloromethane, washed with 100 cm$^3$ of water and then with 50 cm$^3$ of a saturated solution of sodium chloride, dried over magnesium sulphate, and concentrated to dryness under reduced pressure (2.7 kPa). The residue is crystallized from 40 cm$^3$ of ethyl ether. The crystals obtained are drained and dried. 8.4 g of (3aR,4S,7aR)-7,7-diphenyl-2-tert-butyloxycarbonyl-4-perhydroisoindolol are obtained in the form of white crystals; melting point 190° C. The crystallization mother liquors are concentrated to dryness under reduced pressure (2.7 kPa). The residue is chromatographed on a silica gel column (particle size 0.04–0.06 mm, diameter 4 cm, height 33 cm), eluting under a nitrogen pressure of 0.4 bar with a dichloromethane and methanol mixture (96/4 by volume) and collecting fractions of 20 cm$^3$. Fractions 18 to 21 are pooled and concentrated to dryness under reduced pressure (2.7 kPa). 1.88 g of (3aR,4R,7aR)-7,7-diphenyl-2-tert-butyloxycarbonyl-4-perhydroisoindolol are obtained in the form of a white meringue. Fractions 26 to 31 are pooled and concentrated to dryness under reduced pressure (2.7 kPa). The residue is crystallized from 5 cm$^3$ of ethyl ether. 2.88 g of (3aR,4S,7aR)-7,7-diphenyl-tert-butyloxycarbonyl-4-perhydroisoindolol are additionally obtained in the form of white crystals; melting point 190° C.

(3aR,7aR)-7,7-Diphenyl-2-tert-butyloxycarbonyl-4-perhydroisoindolone may be obtained in the following manner:

0.74 g of 4-dimethylaminopyridine and then 14.7 g of di-tert-butyl dicarbonate are successively added to a solution of 20 g of (3aR,7aR)-7,7-diphenyl-4-perhydroiso-indolone hydrochloride in 100 cm$^3$ of dry dichloromethane and 6.17 cm$^a$ of triethylamine. The reaction mixture is stirred for 24 hours at room temperature and then washed with an aqueous solution of citric acid and then with an aqueous solution of sodium hydrogen carbonate, dried over magnesium sulphate, filtered and concentrated to dryness under reduced pressure (2.7 kPa). The residue is crystallized from 90 cm$^3$ of ethyl ether. The crystals are drained, washed with 10 cm$^3$ of ethyl ether and then dried. 14.1 g of (3aR,7aR)-7,7-diphenyl-2-tert-butyloxycarbonyl-4-perhydroisoindolone are obtained in the form of white crystals; melting point 119° C.

EXAMPLE 14

0,766 g of 1-(3-dimethylaminopropyl)-3-ethylcarbodiimide is added to a solution, cooled to 10° C., of 1 g of (3aR,4S,7aR)-7,7-diphenyl-4-perhydroisoindolol, 0.97 g of 2-(3-dimethylaminopropoxy)phenylacetic acid and 0.05 g of 1-hydroxybenzotriazole in 50 cm$^3$ of dichloromethane. The reaction mixture is stirred for 90 minutes 20° C. and then washed twice with 50 cm$^3$ of water and with 50 cm$^3$ of a saturated solution of sodium chloride. The organic phase is dried over magnesium sulphate and concentrated to dryness under reduced pressure (2.7 kPa). The residue is chromatographed on a silica gel column (particle size 0.2–0.063 mm, diameter 2.9 cm, height 23 cm), eluting under a nitrogen pressure of 0.7 bar with 1,2-dichloroethane and methanol mixtures (1 liter at 90/10 by volume and 1.5 liters at 70/30 by volume) and collecting fractions of 25 cm$^3$. Fractions 10 to 84 are pooled and concentrated to dryness under reduced pressure (2.7 kPa) to give 1.1 g of (3aR,4S,7aR)-2-{[2-(3-dimethylaminopropoxy)phenyl]-acetyl}-7,7-diphenyl-4-perhydroisoindolol in the form of a cream-colored meringue.

Infrared spectrum (KBr, characteristics bands, cm$^{-1}$): 3080, 3050, 3020, 2940, 2870, 2815, 2765, 1635, 1600, 1490, 1455, 1445, 1245, 1065, 750, 730, 700. Proton NMR spectrum (DMSO-d$_6$) at 433° K.: 1.06 and 1.76 (2mt, 2×1H, CH$_2$ in 5); 2.27 (s, 6H, N(CH$_3$)$_2$); 3.9 (d, J=11, 1H, 1H of CH$_2$ in 3); 6.8 to 7.5 (mt, 14H, aromatics).

A solution of 100 g of 2-hydroxyphenylacetic acid, 75 cm$^3$ of benzyl alcohol and 0.5 g of paratoluenesulphonic acid in 1400 cm$^3$ of toluene is refluxed for 2 hours while removing the water formed. After cooling, treating with 3 g of animal black and filtering, the reaction mixture is concentrated to 150 cm$^3$ and 300 cm$^3$ of isopropyl oxide are added. The crystals obtained by cooling to 0° C. are drained, washed and dried to give 82.5 g of benzyl 2-hydroxyphenylacetate. 174 g of potassium carbonate are added to a solution of 153 g of this ester in a mixture of 500 cm$^3$ of 1,3-dibromopropane and 2500 cm$^3$ of acetonitrile, and the mixture is refluxed for 17 hours. The reaction mixture is cooled, filtered and concentrated to dryness under reduced pressure (2.7 kPa). The residue is taken up in 500 cm$^3$ of ethyl acetate and the organic phase is washed with 400 cm$^3$ of water twice and twice with 250 cm$^3$ of a saturated solution of sodium chloride and then dried and concentrated to dryness under reduced pressure (2.7 kPa). The residue is chromatographed on a silica gel column (particle size 0.2–0.063 mm, diameter 9 cm, height 55 cm), eluting with a cyclohexane and ethyl acetate mixture (95/5 by volume) and collecting fractions of 500 cm$^3$. Fractions 12 to 18 are pooled and concentrated to dryness under reduced pressure (2.7 kPa) to give 90 g of benzyl 2-(3-bromopropoxy)phenyl-acetate in the form of a yellow oil. A solution of 40 g of this product in 500 cm$^3$ of acetonitrile is heated in an autoclave with 27 g of sodium iodide and 90 g of dimethylamine for 16 hours at 80° C. The reaction mixture is cooled, filtered and concentrated to dryness under reduced pressure (2.7 kPa). The residue is purified by acid-base treatment to give 29.3 g of benzyl 2-(3-dimethylaminopropoxy)phenylacetate in the form of a yellow oil. Hydrogenation of this ester, at atmospheric pressure at 40° C. in ethyl acetate in the presence of palladium hydroxide followed by crystallization from ethyl acetate, yield 17.5 g of 2-(3-dimethylaminopropoxy)phenylacetic acid in the form of white crystals; melting point 98° C.

EXAMPLE 15

By carrying out the procedure as in Example 2, but using the hydrochloride salt of [2-(3-isopropylaminopropoxy)phenyl]acetic acid and (3aR,7R,7aR)-4,4-diphenyl-7-fluoroperhydroisoindole hydrochloride, a yellow oil is obtained after purification by chromatography on a Merck silica gel column (particle size 0.04–0.06 mm, diameter 3 cm, height 25 cm), eluting under a nitrogen pressure of 0.5 bar with a dichlormethane and methanol mixture (90/10 by volume) and collecting fractions of 20 cm$^3$. The hydrochloride salt of this oil yields (3aR,7R,7aR)-2-[[[3-(1-isopropylamino)-2-propoxy]phenyl]acetyl]-4,4-diphenyl-7-fluoroperhydroisoindole hydrochloride in the form of a chestnut-colored solid.

Infrared spectrum (KBr, characteristic bands, cm$^{-1}$): 3090+3060+3030, 2950+2885, 2860−2250, 1640, 1605+1495, 1455+1445, 1245, 750+700. Proton NMR spectrum (250 MHz, DMSO, δ in ppm and J in Hz): (at room temperature, a mixture of the two rotamers is observed ); 1 to 1.35 (mt, 1H, axial H of CH$_2$ in 6); 1.18 and 1.25 (2d, J=7, 6H, CH$_3$ isopropyl); 1.8 to 2.1 (mt, H of CH$_2$ in 6 and CH$_2$ in a); 2.27 (broad d, J=13.5, 1H, equatorial H of CH$_2$ in 5); 2.4 to 4 (mt, H of CH$_2$ in 5, CH$_2$ in 3, CH$_2$ in 1, CH in 3a, CH in 7a, NCH); 3.02 (mt, 2H, NCH$_2$ in b); 3.3 to 3.54 (2s, 2H, NCOCH$_2$Ar); 3,9 to 4.15 (mt, 2H, OCH$_2$); 4.76 and 4.8 (broad 2d, J=50, 1H, CHF); 6.7 to 7.5 (mt, 14H, H aromatics).

EXAMPLE 16

By carrying out the procedure as in Example 2, but using the hydrochloride salt of [2-(3-benzylaminopropoxy)phenyl]acetic acid and (3aR,7R,7aR)-4,4-diphenyl-7-fluoroperhydroisoindole hydrochloride, a yellow oil is obtained after purification by chromatography on a Merck silica gel column (particle size 0.04–0.06 mm, diameter 3 cm, height 25 cm), eluting under a nitrogen pressure of 0.5 bar with an ethyl acetate and methanol mixture (95/5 by volume) and collecting fractions of 20 cm$^3$. The acid oxalate of this oil yields (3aR,7R,7aR)-2-[[[3-(1-benzylamino)-2-propoxy]phenyl]acetyl]-4,4-diphenyl-7-fluoroperhydroisoindole, acid oxalate in the form of a chestnut-coloured solid.

Infrared spectrum (KBr, characteristic bands, cm$^{-1}$): 3090+3060+3030, 2955+2885, 3250−2250, 1780+1720, 1640, 1625, 1605+1498, 1455+1445, 1245, 750+700. Proton NMR spectrum (250 MHz, DMSO, δ in ppm and J in Hz): (at room temperature, a mixture of the two rotamers is observed); 1 to 1.4 (mt, 1H, axial H of CH$_2$ in 6); 1.8 to 4.2 (mt, other H of CH$_2$ in 6, CH$_2$ in 5, CH$_2$ in 3, CH$_2$ in 1, CH in 3a and CH in 7a, OCH$_2$—CH$_2$—CH$_2$N); 3.27 and 3.53 (2s, 2H, HCOCH$_2$Ar); 4.1 and 4.18 (2s, 2H, NCH2Ar), 4.78 and 4.81 (2dmt, J=50, 1H, CH—F); 6.7 to 7.6 (mt, 19H, aromatics).

EXAMPLE 17

By carrying out the procedure as in Example 2, but using 1.26 g of the hydrochloride salt of [2-(3-diethylaminopropoxy)phenyl]acetic acid and 1.2 g of (3aR,7R,7aR)-4,4-diphenyl-7-fluoroperhydroisoindole hydrochloride, 1.5 g of (3aR,7R,7aR)-2-{[2-(3-diethylaminopropoxy)phenyl]acetyl}-4,4-diphenyl-7-fluoroperhydroisoindole hydrochloride are obtained, after purification by chromatography on a silica gel column, in the form of a white solid.

Infrared spectrum (KBr, characterisic bands, cm$^{-1}$): 3090, 3060, 3030, 2950, 2885, 2800, 2200, 1640, 1600, 1498, 1455, 1250, 1050, 750, 700. Proton NMR spectrum (250 MHz, DMSO-d$_6$+CD$_3$COOD, at room temperature, a mixture of the two rotamers is observed): 1 to 1.35 (mt, 1H, axial H-6); 1.18 and 1.23 (2t, J=6.5, 6H in total, —CH$_2$CH$_3$); 1.8 to 2.2 (mt, 3H, H-6' and CH$_2$—CH$_2$—CH$_2$); 2.26 (broad d, J=13.5, 1H, equatorial H in 5); 2.4 to 4 (mt, 6H, CH$_2$ in 1, CH$_2$ in 3, H-3a and H-7a); 2.8 (td, J=13.5 and 3, 1H, axial H-5); 3 to 3.2 (mt, 6H, CH$_2$—N(CH$_2$CH$_3$)$_2$); 3.3 and 3.53 (2s, 2H, =NCOCH$_2$Ar); 3.9 to 4.1 (mt, 2H, OCH$_2$); 4.76 and 4.81 (broad 2d, J=50, 1H in total, =CHF); 6.7 to 7.5 (mt, 14H, aromatics).

The hydrochloride salt of [2-(3-diethylaminopropoxy)phenyl]acetic acid may be prepared by carrying out the procedure as described in Example 20, using 1.24 g of methyl [2-(3-diethylaminopropoxy)phenyl]acetate and 20 cm$^3$ of 6N hydrochloric acid. 1.26 g of the hydrochloride salt of [2-(3-diethylaminopropoxy)phenyl]acetic acid are obtained in the form of a light chestnut-colored solid.

Infrared spectrum (KBr, characteristic bands, cm$^{-1}$): 3250–2250, 3100–3000, 3000–2850, 1722, 1600, 1585, 1495, 1472, 1450, 1385, 1250, 760. Proton NMR spectrum (250 MHz, DMSO-d$_6$): 1.25 (t, J=7.5, 6H, 2×CH$_2$CH$_3$); 2.14 (mt, 2H, CH$_2$—CH$_2$—CH$_2$); 3.05 to 3.3 (mt, 6H, CH$_2$—N(CH$_2$CH$_3$)$_2$); 3.53 (2s, 2H, CH$_2$COO); 4.08 (t, J=6, 2H, OCH$_2$); 6.33 (mt, 2H, aromatics in 3 and 5); 7.23 (mt, 2H, aromatics in 4 and 6); 10.62 (mf, 1H, —NH$^+$<); 12.2 (mf, 1H, COOH).

Methyl [2-(3-diethylaminopropoxy)phenyl]acetate may be prepared as described in Example 20, using 1.8 g of methyl 2-(3-bromopropoxy)phenylacetate and 0.66 cm$^3$ of diethylamine. 1.24 g of methyl [2-(3-diethylaminopropoxy)phenyl]acetate are obtained, after purification by chromatography on a silica gel column, in the form of an orange-colored oil which crystallizes at room temperature.

Infrared spectrum (CCl$_4$, characteristic bands, cm$^{-1}$): 3070, 3030, 2970, 2930, 2875, 2800, 1740, 1605, 1590, 1495, 1475, 1455, 1435, 1250. Proton NMR spectrum (250 MHz, CDCl$_3$): 1.10 (t, J=7.5, 6H, 2×CH$_2$CH$_3$); 1.96 (mt, 2H, CH$_2$—CH$_2$—CH$_2$); 2.62 (q, J=7, 4H, N(CH$_2$CH$_3$); 2.68 (t, J=7, 2H, CH$_2$—NEt$_2$); 3.64 (2s, 2H, CH$_2$COO); 3.7 (s, 3H, COOCH$_3$); 4.03 (t, J=6, 2H, OCH$_2$); 6.9 (mt, 2H, aromatics in 3 and 5); 7.22 (mt, 2H, aromatics in 4 and 6).

EXAMPLE 18

By carrying out the procedure as in Example 2, but using 1.37 g of {3-[N-(2-hydroxyethyl)-N-methylamino]-2-propoxy}phenylacetic acid and 1.2 g of (3aR, 7R, 7aR)-4,4-diphenyl-7-fluoroperhydroisoindole hydrochloride, 0.86 g of (3aR,7R,7aR)-2-{{3-[N-(2-hydroxyethyl)-N-methylamino]-2-propoxy}phenylacetyl}-4,4-diphenyl-7-fluoroperhydroisoindole is obtained, after purification by chromatography on a silica gel column, in the form of a white meringue.

Infrared spectrum (KBr, characteristic bands, cm$^{-1}$): 3425, 3105, 3090, 3060, 3030, 2950, 2885, 2850, 2800, 1640, 1600, 1495, 1455, 1445, 1250, 1050, 755, 700. Proton NMR spectrum (400 MHz, DMSO-d$_6$+CD$_3$COOD-d$_4$, at 303° K.): (at this temperature, a mixture of rotamers is observed); 1.14 (broad dt, J=46 and 13.5, 1H, axial H-6); 1.85 (mt, 1H, equatorial H-6); 2.03 (mt, 2H, CH$_2$—CH$_2$—CH$_2$); 2.20 (mt, 1H, H-5); 2.3 to 3.8 (mt, H-5′, CH$_2$—1 and CH$_2$—3, H-7a and H-3a, >NCOCH$_2$Ar, —CH$_2$—N—CH$_2$CH$_2$O—); 2.75 and 2.80 (2s, 3H, >N—CH$_3$); 3.8 to 4 (mt, 2H, ArOCH$_2$); 4.7 and 4.74 (2 dmt, J=50, 1H, CHF); 6.7 to 7.4 (mt, 14H, aromatics).

{3-[N-(2-Hydroxyethyl)-N-methylamino]-2-propoxy}phenylacetic acid may be prepared by carrying out the procedure as described in Example 20, using 2.1 g of methyl {{3-[N-(2-hydroxyethyl)-N-methylamino]2-propoxy}phenyl}acetate and 30 cm$^3$ of 6N hydrochloric acid. 2.27 g of {3-[N-(2-hydroxyethyl)-N-methylamino]2-propoxy}phenylacetic acid are obtained in the form of a red oil.

Infrared spectrum (between cover glasses, characteristic bands, cm$^{-1}$): 1725, 1605, 1590, 1498, 1475, 1455, 1465, 1250, 1055, 760. Proton NMR spectrum (400 MHz, DMSO-d$_6$, 383° K.): 1.98 (qt, J=6.5, 2H, CH$_2$—C$_2$—CH$_2$); 2.84 (s, 3H, >N—CH$_3$); 3.15 to 3.4 (mt, 4H, NCH$_2$); 3.56 (s, 2H, CH$_2$COO); 3.84 (t, J=6, CH$_2$OH); 4.1 (t, J=6.5, ArOCH$_2$); 6.96 (mt, 2H, aromatics in 3 and 5); 7.24 (mt, 2H, aromatics in 4 and 6).

Methyl {{3-[N-(2-hydroxyethyl)-N-methylamino]-2-propoxy}phenyl}acetate may be prepared as described in Example 20, using 1.8 g of methyl 2-(3-bromopropoxy)phenylacetate and 0.5 cm$^3$ of 2-(methylamino)-ethanol. 0.5 g of methyl {{3-[N-(2-hydroxyethyl)-N-methylamino]-2-propoxy}phenyl}acetate is obtained, after purification by chromatography on a silica gel column, in the form of a pinkish oil.

Infrared spectrum (CH$_2$Cl$_2$, characteristic bands, cm$^{-1}$): 3460, 3050, 3030, 3000–2850, 2810, 1738, 1600, 1590, 1498, 1455, 1435, 1250. Proton NMR spectrum (250 MHz, CDCl$_3$): 2.07 (mt, 2H, CH$_2$—CH$_2$—CH$_2$); 2.2 to 2.8 (mf, 1H, OH); 2.43 (s, 3H, >N—CH$_3$); 2.72 (t, J=5.5, 2H, NCH$_2$CH$_2$OH); 2.76 (t, J=7, 2H, CH$_2$N); 3.64 (s, 2H, CH$_2$COO); 3.71 (s, 3H, CO$_2$C$_3$); 3.71 (t, J=5.5, CH$_2$OH); 4.04 (t, J=6, ArOCH$_2$); 6.32 (mt, 2H, aromatics in 3 and 5); 7.24 (mt, 2H, aromatics in 4 and 6).

EXAMPLE 19

By carrying out the procedure as in Example 2, but using 1.5 g of the hydrochloride salt of [2-(3-diisopropylaminopropoxy)phenyl]acetic acid and 1.3 g of (3aR,7R,7aR)-4,4-diphenyl-7-fluoroperhydroisoindole hydrochloride, 1.57 g of (3aR,7R,7aR)-2-{[2-(3-diisopropylamino-propoxy)phenyl]acetyl}-4,4-diphenyl-7-fluoroperhydro-isoindole hydrochloride are obtained, after purification by chromatography on a silica gel column, in the form of a white solid.

Infrared spectrum (KBr, characteristic bands, cm$^{-1}$): 3090, 3060, 3030, 2950, 2855, 2800–2200, 1640, 1605, 1495, 1455, 1445, 1247, 755, 700. Proton NMR spectrum (250 MHz, DMSO-d$_6$+CD$_3$COOD, at room temperature, a mixture of the two rotamers is observed): 1 to 1.4 (mt, 1H, axial H-6); 1.2 to 1.4 (mt, 12H, isopropyl —CH$_3$); 1.8 to 2.2 (mt, 3H, H-6′ and CH$_2$—CH$_2$—CH$_2$); 2.25 (broad d, J=13.5, 1H, equatorial H-5); 2.4 to 4 (mt, H-5′, CH$_2$-3, CH$_2$—1, H-3a, H-7a and —N(CH(CH$_3$)$_2$)$_2$); 3.15 (mt, 2H, —CH$_2$N<); 3.3 and 3.55 (2s, 2H, >NCOCH$_2$Ar); 3.9 to 4.1 (mt, 2H, OCH$_2$); 4.75 and 4.79 (2d, J=50, 1H, CHF); 6.7 to 7.5 (mt, 13H, aromatics).

The hydrochloride salt of [2-(3-diisopropylaminopropoxy)phenyl]acetic acid may be prepared by carrying out the procedure as described in Example 20, using 1.50 g of methyl [2-(3-diisopropylaminopropoxy)-phenyl]-acetate and 30 cm$^3$ of 6N hydrochloric acid. 1.5 g of the hydrochloride salt of [2-(3-diisopropyl-aminopropoxy)-phenyl]acetic acid are obtained in the form of a chestnut-colored oil.

Infrared spectrum (KBr, characteristic bands, cm$^{-1}$): 3500–2250, 3100–3000, 3000–2850, 1727, 1605, 1595, 1500, 1470, 1455, 1425, 1250, 760. Proton NMR spectrum (250 MHz, DMSO-d$_6$): 1.31 and 1.36 (2d, J=6.5, 12H, isopropyl —CH$_3$); 2.2 (mt, 2H, CH$_2$—CH$_2$—CH$_2$); 3.21 (mt, J=7, 2H, —CH$_2$N<); 3.53 (s, 2H, >NCOCH$_2$Ar); 3.61 (mt, 2H, —N(CH(CH$_3$)$_2$)$_2$); 4.07 (t, J=6, 2H, OCH$_2$); 6.91 (mt, 2H, aromatics in 3 and 5); 7.22 (mt, 2H, aromatics in 4 and 6); 9.98 (mf, 1H, —NH$^+$<).

Methyl [2-(3-diisopropylaminopropoxy)phenyl]acetate may be prepared as described in Example 20, using 2.65 g of methyl 2-(3-bromopropoxy)phenylacetate and 1.98 cm$^3$ of diisopropylamine. 1.31 g of methyl [2-(3-diiso-propylaminopropoxy)phenyl]acetate are obtained in the form of a yellow oil.

Infrared spectrum (CCl$_4$, characteristic bands, cm$^{-1}$): 3070, 3050, 3030, 2970, 2930, 2875, 1743, 1605, 1590, 1495, 1470, 1455, 1435, 1385, 1360, 1250. Proton NMR spectrum (250 MHz, DMSO-d$_6$): 0.97 (d, J=7, 12H, isopropyl —CH$_3$); 1.72 (quintuplet, J=7, 2H, CH$_2$—CH$_2$—CH$_2$); 2.55 (t, J=7, 2H, —CH$_2$N<); 2.97 (mt, 2H, —N(CHMe)$_2$); 3.59 and 3.62 (2s, 5H, >NCOCH$_2$Ar and CO$_2$CH$_3$); 3.97 (t, J=7, 2H, OCH$_2$); 6.32 (mt, 2H, aromatics in 3 and 5); 7.22 (mt, 2H, aromatics in 4 and 6).

EXAMPLE 20

By carrying out the procedure as in Example 2, but using 1.45 g of the hydrochloride salt of [2-(3-piperidinopropoxy)phenyl]acetic acid and 1.30 g of (3aR,7R,7aR)-4,4-diphenyl-7-fluoroperhydroisoindole hydrochloride, 1.44 g of (3aR,7R,7aR)-2-{[2-(3-piperidinopropoxy)phenyl]acetyl}-4,4-diphenyl-7-fluoroperhydroisoindole hydrochloride are obtained, after purification by chromatography on a silica gel column, in the form of a white solid.

Infrared spectrum (KBr, characteristic bands, cm$^{-1}$): 3090, 3060, 3030, 2955, 2885, 2800−2200, 1640, 1605, 1498, 1455, 1445, 1250, 755, 700. Proton NMR spectrum (250 MHz, DMSO-d$_6$ at 433° K.): 1.27 (broad dt, J=46 and 13.5, axial H-6); 1.5 to 2.1 (mf, 7H, N(CH$_2$CH$_2$)$_2$CH$_2$ and H-6'); 2.23 (mt, 2CH$_s$—CH$_2$—CH$_2$); 2.32 (broad d, J=13.5, 1H, equatorial H-5); 2.64 (td, J=13.5 and 3, 1H, axial H-5); 2.7 to 4 (mt, CH$_2$-1, CH$_2$-3, H-3a, H-7a and N(CH$_2$CH$_2$)$_2$CH$_2$); 3.13 (t, J=7.5, 2H, —CH$_2$N<); 3.79 (AB, 2H, NCOCH$_2$Ar); 4.08 (mf, 2H, OCH$_2$); 4.82 (broad d, J=50, 1H, CHF); 6.8 to 7.5 (mt, 14H, aromatics).

The hydrochloride salt of [2-(3-piperidinopropoxy)phenyl]acetic acid may be prepared in the following manner:

A 6N solution of hydrochloric acid is added to 2.0 g of methyl [2-(3-piperidinopropoxy)phenyl]acetate. After refluxing for 3 hours, the solution is concentrated to dryness at 50° C. under reduced pressure. The residue is then taken up in 30 cm$^3$ of toluene and then the solution is concentrated to dryness. After another treatment with toluene, 1.9 g of the hydrochloride salt of [2-(3-piperidinopropoxy)phenyl]acetic acid are obtained in the form of a white solid which is used as it is in the next stage.

Methyl [2-(3-piperidinopropoxy)phenyl]acetate may be prepared in the following manner:

1.51 g of potassium carbonate, 0.3 g of sodium iodide and then 1.0 cm$^3$ of piperidine are successively added to a solution of 2.87 g of methyl [2-(3-bromopropoxy)-phenyl]acetate in 30 cm$^3$ of acetonitrile. The reaction mixture is refluxed for 2 hours and then filtered. The filtrate is concentrated to dryness and the residue obtained is chromatographed on a silica gel column (particle size 0.04–0.06 mm, diameter 4 cm, height 50 cm), eluting under a nitrogen pressure of 0.1 bar with an ethyl acetate and methanol mixture (80/20 by volume) and collecting fractions of 125 cm$^3$. Fractions 9 to 16 are pooled and concentrated to dryness. The residue is triturated in diisopropyl oxide, the suspension is filtered and the filtrate is concentrated to dryness under reduced pressure (2.7 kPa). 2.0 g of methyl [2-(3-piperidinopropoxy)phenyl]-acetate are obtained in the form of a yellow oil which is used as it in the next stage.

EXAMPLE 21

By carrying out the procedure according to that of Example [RP74066], using 1.65 g of (3aR,7R,7aR)-4,4-diphenyl-7-fluoroperhydroisoindole hydrochloride and 1.5 g of {2-[3-(2-hydroxymethyl-(S)-1-pyrrolidinyl)-propoxy]phenyl}acetic acid in 160 cm$^3$ of dry dichloromethane, 1.27 g of (3aR,7R,7aR)-4,4-diphenyl-7-fluoro-2-{{2-[3-(2-hydroxymethyl-(S)-1-pyrrolidinyl)-propoxy]phenyl}acetyl}perhydroisoindole hydrochloride are obtained in the form of a white meringue.

Proton NMR spectrum: 1.27 (broad dt, J=46 and 13.5; 1H, axial H of —CH$_2$— in 6); 1.8 to 2.4 (mt, the other H of —CH$_2$— in 6 and —CH$_2$—of pyrrolidine); 2.3 (broad d, J=13.5; 1H, equatorial H of —CH$_2$— in 5); 2.66 (mt, the other H of —CH$_2$— in 5); 2.4 to 4 (mt, —CH$_2$— in 1, —CH$_2$— in 3, CH in 3a, CH in 7a and CH$_2$N); 3.85 (limiting ab, NCOCH$_2$); 4 to 4.3 (mt, 4H, —CH$_2$—O); 4.84 (broad d, J=50, 1H, CHF); 6.8 to 7.6 (mt, 13H, aromatics). Infrared spectrum (KBr): 3420, 3105−3090−3060−3030, 2955−2885, 2800−2200, 1640, 1605−1498, 1455−1445, 1250, 1065, 1050, 755−705.

2-[3-(2-Hydroxymethyl-(S)-1-pyrrolidinyl)propoxy]-phenylacetic acid may be obtained in the following manner:

A suspension of 1.65 g of methyl 2-[3-(2-hydroxymethyl-(S)-1-pyrrolidinyl)propoxy]phenylacetate in 20 cm$^3$ of 6N hydrochloric acid is refluxed for 3 hours. The reaction mixture is concentrated to dryness under reduced pressure (2.7 kPa). The residue obtained is triturated in ether. 1.45 g of 2-[3-(2-hydroxymethyl-(S)-1-pyrrolidinyl)propoxy]phenylacetic acid are obtained in the form of a brown oil.

Proton NMR spectrum: 1.7 to 2.3 (mt, 6H, —CH$_2$— of pyrrolidine); 3 to 3.3 and 3.4 to 3.7 (2mt, 5H in total NCH$_2$ and NCH); 3.54 (s, 2H, CH$_2$COO); 3.76 (split ab, J=12.5 and 4, 2H, CH$_2$O); 4.06 (mt, 2H, ArOCH$_2$); 6.94 (mt, 2H, aromatics in ortho and para of OR); 7.22 (mt, 2H, aromatics in meta of OR); 10.35 (mt, 1H, NH+$^{Cl-}$).

Methyl 2-[3-(2-hydroxymethyl-(S)-1-pyrrolidinyl)-propoxy]phenylacetate may be obtained in the following manner:

0.92 g of potassium carbonate, 0.22 g of sodium iodide and then 0.63 g of 2-hydroxymethyl-(S)-pyrrolidine are successively added to a solution of 1.8 g of methyl 2-(3-bromopropoxy)phenylacetate in 20 cm$^3$ of acetonitrile. The reaction mixture is heated at 70° C. for 5 hours and then, after cooling, diluted with 100 cm$^3$ of dichloromethane, washed with 100 cm$^3$ of water and then with 100 cm$^3$ of a saturated aqueous solution of sodium chloride, dried over magnesium sulphate and concentrated to dryness under reduced pressure (2.7 kPa). The residue is chromatographed on a Merck silica gel column (particle size 0.04–0.06 mm, diameter 3 cm, height 30 cm), eluting under a nitrogen pressure of 0.4 bar with an ethyl acetate and methanol mixture (90/10 by volume) and collecting fractions of 100 cm$^3$. Fractions 7 to 20 are pooled and concentrated to dryness under reduced pressure (2.7 kPa). 1.55 g of methyl 2-[3-(2-hydroxymethyl-(S)-1-pyrrolidinyl)propoxy]-phenylacetate are obtained in the form of an oil.

Proton NMR spectrum: 1.5 to 2 (mt, 4H, CH$_2$ of pyrrolidine); 1.84 (mt, 2H, CH$_2$ of the propoxy chain); 2.2 and 3.08 (2mt, 1H each, NCH$_2$ of pyrrolidine); 2.4 and 2.35 (mt, 1H each, NCH$_2$); 2.5 (mt, 1H, NCH of pyrrolidine); 3.22 (dd, J=11.5 and 6.5, 1H of CH$_2$O); 3.44 (dd, J=11.5 and 4.5, 1H, the other H of CH$_2$O); 3.6 (2s, 5H, CH$_2$COOCH$_3$); 4 (t, J=6, 2H, ArOCH$_2$); 6.92 (mt, 2H, aromatics in ortho and para of OR); 7.22 (mt, 2H, aromatics in meta of OR).

EXAMPLE 22

By carrying out the procedure as in Example 2, but using 2.3 g of the hydrochloride salt of {[3-(delta$^3$-1- pyrrolinyl)-2-propoxy]phenyl}acetic acid and 2.32 g of (3aR,7R,7aR)-4,4-diphenyl-7-fluoroperhydroisoindole hydrochloride, 3.4 g of a crude product are obtained in the form of a white meringue. This product is taken up in 100 cm$^3$ of ethyl acetate, the solution obtained is washed with 40 cm$^3$ of a 5% aqueous solution of sodium bicarbonate, followed by extraction first with 30 cm$^3$, then with 20 cm$^3$ of 1N hydrochloric acid. The acidic aqueous extracts are pooled, alkalized with 4N sodium hydroxide and then extracted again with twice 50 cm$^3$ of ethyl acetate. The organic phase is concentrated to dryness under reduced pressure (2.7 kPa), the residue is chromatographed on a SEPHADEX LH-20 column (diameter 3 cm, height 1.4 m), eluting with methanol and collecting fractions of 13 cm$^3$. Fractions 35 to 38 are pooled and concentrated to dryness under reduced pressure (2.7 kPa). The residue is triturated in ethyl ether, the solid is drained and dried under reduced pressure (2.7 kPa). 0.49 g of (3aR,7R,7aR)-2-{{[3-(delta$^3$-1-pyrrolinyl)-2-propoxy]phenyl}acetyl}-4,4-diphenyl-7-fluoroperhydroisoindole hydrochloride is obtained in the form of a white solid.

Infrared spectrum (KBr, characteristic bands, cm$^{-1}$): 3090, 3060, 3030, 2945, 2880, 2800−2200, 1640, 1600, 1495, 1455, 1445, 1245, 755, 700. Proton NMR spectrum (200 MHz, DMSO-d$_6$+CD$_3$COOD at 413° K.): 1.32 (broad dt, J=46 and 13.5, 1H, axial H-6); 2.05 (mt, 1H, equatorial H-6); 2.15 (qt, J=7, 2H, CH$_2$—CH$_2$—CH$_2$); 2.3 (broad d, J=13.5, 1H, equatorial H-5); 2.67 (td, J=13.5 and 3, 1H, axial H-5); 2.6 to 3.9 (mt, CH$_2$-3, CH$_2$-1, H-3a and H-7a); 3.35 (t, J=7, 2H, —CH$_2$N<); 3.8 (limiting AB, 2H, >NCOCH$_2$Ar); 4.07 (s, 4H, —N(CH$_2$CH)$_2$); 4.10 (t, J=7, 2H, CH$_2$O); 4.8 (dmt, J=50, 1H, CHF); 5.91 (s, 2H, CH=CH); 6.8 to 7.5 (mt, 14H, aromatics).

The hydrochloride salt of {[3-(delta$^3$-1-pyrrolinyl)-2-propoxy]phenyl}acetic acid may be prepared by carrying out the procedure as described in Example 20, using 8 g of methyl {[3-(delta$^3$-1-pyrrolinyl)-2-propoxy]phenyl}acetate and 100 cm$^3$ of 6N hydrochloric acid. 4.6 g of {[3-(delta$^3$-1-pyrrolinyl)-2-propoxy]phenyl}-acetic hydrochloride are obtained in the form of a light beige solid; melting point 140° C.

Methyl {[3-(delta$^3$-1-pyrrolinyl)-2-propoxy]phenyl}acetate may be prepared as described in Example 20, using 15.6 g of methyl 2-(3-bromopropoxy)phenylacetate and 3.8 g of delta$^3$-pyrroline. 8.0 g of methyl {[3-(delta$^3$-1-pyrrolinyl)-2-propoxy]phenyl}acetate are obtained, after purification by chromatography on a silica gel column, in the form of an orange-yellow oil.

Proton NMR spectrum (300 MHz, CDCl$_3$): 1.98 (mt, 2H, CH$_2$—CH$_2$—CH$_2$); 2.81 (t, J=7, 2H, —CH$_2$N<); 3.51 (s, 4H, —N(CH$_2$CH)$_2$); 3.64 (s, 2H, >NCOCH$_2$Ar); 3.7 (s, 3H, CO$_2$CH$_3$); 4.06 (t, J=6.5, 2H, CH$_2$O); 5.8 (s, 2H, CH=CH); 6.9 (mt, 2H, aromatics in 3 and 5); 7.21 (mt, 2H, aromatics in 4 and 6).

EXAMPLE 23

A solution of 1.32 g of (3aR,4S,7aR)-2-[(2methoxyphenyl)acetyl]-7,7-diphenyl-4-perhydroisoindolol in 100 cm$^3$ of anhydrous dichloromethane is added over 20 minutes to a solution, cooled to 0° C., of 0.4 cm$^3$ of 4-trifluorothiomorpholine in 20 cm$^3$ of anhydrous dichloromethane. After stirring for 2 hours at 20° C., the reaction mixture is washed with 100 cm$^3$ of a 5% w/v aqueous solution of sodium bicarbonate, dried over magnesium sulphate and concentrated to dryness under reduced pressure (2.7 kPa). The residue is chromatographed on a silica gel column (particle size 0.04–0.06 mm, diameter 2.5 cm, height 30 cm), eluting under a nitrogen pressure of 0.5 bar with a cyclohexane and ethyl acetate mixture (50/50 by volume) and collecting fractions of 30 cm$^3$. Fractions 10 to 20 are pooled and concentrated to dryness under reduced pressure (2.7 kPa). The residue is washed with ethyl ether and then with diisopropyl oxide, the solid is drained and dried. 0.38 g of (3aR,7R,7aR)-2-[(2-methoxyphenyl)-acetyl]-4,4-diphenyl-7-fluoroperhydroisoindole is obtained in the form of a white solid; melting point 205° C.

EXAMPLE 24

A solution of 0.91 g of 2-[(2-dimethylaminophenyl)-acetyl]-7,7-diphenyl-4-perhydroisoindolol, a mixture of the (3aR,4S,7aR) and (3aR,4R,7aR) isomers (the 3aR,4S,7aR isomer being very predominant), obtained according to Example 17, in 30 cm$^3$ of anhydrous dichloromethane is added over 20 minutes, under a nitrogen atmosphere, to a solution, cooled to 10° C., of 0.27 cm$^3$ of 4-trifluorothiomorpholine in 10 cm$^3$ of anhydrous dichloromethane. After stirring for 2 hours at 20° C. the reaction mixture is successively washed with 25 cm$^3$ of water and 20 cm$^3$ of a 0.1 N aqueous solution of sodium hydroxide, and then dried over magnesium sulphate and concentrated to dryness under reduced pressure (2.7 kPa). The residue is chromatographed on a Merck silica gel column (particle size 0.04–0.06 mm, diameter 2 cm, height 40 cm), eluting under a nitrogen pressure of 0.5 bar with a cyclohexane and ethyl acetate mixture (70/30 followed by 50/50 by volume) and collecting fractions of 20 cm$^3$. Fractions 22 to 25 are pooled and concentrated to dryness under reduced pressure (2.7 kPa). The residue is washed with 10 cm$^3$ of diisopropyl oxide, the solid is drained and dried. 0.12 g of (3aR,7R,7aR)-2-[(2-dimethylaminophenyl)-acetyl]-4,4-diphenyl-7-fluoroperhydroisoindole is obtained in the form of a white solid; melting point 186° C.

EXAMPLE 25

A solution of 0.15 g of sodium borohydride and 0.05 cm$^3$ of an aqueous solution of sodium hydroxide (at 30%) in 30 cm$^3$ of methanol is added over 10 minutes to a suspension, cooled to 5° C., of 3.0 g of (3aR,7aR)-2-[(2-dimethylaminophenyl)acetyl]-7,7-diphenyl-4-perhydroisoindolone in 150 cm$^3$ of methanol. After stirring for 2 hours at 5° C., the reaction mixture is concentrated to a reduced volume (about 30 cc) and taken up in 150 cm$^3$ of dichloromethane. The solution obtained is washed with 50 cm$^3$ of water, dried over magnesium sulphate and concentrated to dryness at 50° C. under reduced pressure (2.7 kPa). The residue is crystallized from 10 cm$^3$ of acetonitrile, the crystals are drained, washed with acetonitrile and dried. 2.2 g of a mixture (2.2 g) of (3aR,4S,7aR)-2-[(2-dimethylaminophenyl)-acetyl]-7,7-diphenyl-4-perhydroisoindolol and (3aR,4R,7aR)-2-[(2-dimethylaminophenyl)acetyl]-7,7-diphenyl-4-perhydroisoindolol, are obtained in the form of a white solid; melting point 156° C.

EXAMPLE 26

A solution of 0.12 g of sodium borohydride and 0.05 cm$^3$ of 10N sodium hydroxide in 20 cm$^3$ of methanol is added over 10 minutes to a suspension, cooled to +5° C., of 2.0 g of (3aRS,7aRS)-7,7-diphenyl-2-phenylacetyl-4-perhydro-isoindolone in 100 cm$^3$ of methanol. The reaction mixture is stirred for 2 hours at low temperature, followed by the addition of 0.5 cm$^3$ of 1N hydrochloric acid and concentration to a reduced volume, at 40° C. under reduced pressure (2.7 kPa). The residue is taken up in 50 cm³ of water and 150 cm³ of dichloromethane. After stirring, the organic phase is dried over magnesium sulphate and concentrated to dryness. The solid is crystallized from acetonitrile, the crystals are washed with acetonitrile and diisopropyl oxide, drained and then dried. 0.24 g of (3aRS,4RS,7aRS)-7,7-diphenyl-2-phenyl-acetyl-4-perhydroisoindolol is obtained in the form of white crystals; melting point 220° C.

EXAMPLE 27

The filtrate from the crystallization of the product obtained in the example above is concentrated to dryness. The residue is chromatographed on a silica gel column (particle size 0.04–0.06 mm, diameter 2 cm, height 35 cm), eluting under a nitrogen pressure of 0.5 bar with a 1,2-dichloroethane and methanol mixture (95/5 by volume) and collecting fractions of 50 cm³. Fractions 14 to 17 are pooled and concentrated to dryness under reduced pressure (2.7 kPa). 0.28 g of (3aRS,4SR,7aRS)-7,7-diphenyl-2-phenylacetyl-4-perhydroisoindolol is obtained in the form of white crystals; melting point 222° C.

EXAMPLE 28

A solution of 0.6 g of (3aR,7R,7aR)-4,4-diphenyl-7-fluoroperhydroisoindole hydrochloride and 0.51 cm³ of triethylamine in 10 cm³ of dry dichloromethane is added to a solution of 0.41 g of ethyl (2-methoxyphenyl)-acetimidate tetrafluoroborate in 10 cm³ of dry dichloromethane. The reaction mixture is refluxed for 3 hours. It is then treated, after re-equilibrating to room temperature, with 5 cm³ of a 10% aqueous solution of potassium carbonate; the organic phase is washed with 10 cm³ of distilled water, dried over magnesium sulphate and concentrated to dryness under reduced pressure (2.7 kPa). The residue is chromatographed on a silica gel column (particle size 0.04–0.06 mm, diameter 2 cm, height 20 cm), eluting under a nitrogen pressure of 0.6 bar with an ethyl acetate, acetic acid and water mixture (15/1/1 by volume) and collecting fractions of 25 cm³. Fractions 24 to 38 are pooled and concentrated to dryness under reduced pressure (2.7 kPa). The residue is taken up in 40 cm³ of dichloromethane, washed with 10 cm³ of a saturated aqueous solution of potassium carbonate and then with 10 cm³ of a saturated aqueous solution of sodium chloride. The organic phase is dried over magnesium sulphate and concentrated to dryness under reduced pressure (2.7 kPa). The residue is crystallized from isopropyl oxide. The crystals are drained and dried. 0.18 g of (3aR,7R,7aR)-4,4-diphenyl-7-fluoro-2-[1-imino-2-(2-methoxyphenyl)ethyl]perhydroisoindole is obtained in the form of white crystals, melting point 184° C., with decomposition.

EXAMPLE 29

A solution of 1.56 g of ethyl (2-methoxyphenyl)-acetimidate tetrafluoroborate and 0.96 cm³ of triethylamine in 20 cm³ of dry dichloromethane is added to a solution of 2 g of (3aR,4S,7aR)-7,7-diphenyl-4-perhydroisoindolol in 30 cm³ of dry dichloromethane, and the reaction mixture is then refluxed for 2 hours. 10 cm³ of a 10% aqueous solution of potassium carbonate are then added, the mixture is decanted and then the organic phase is washed with 20 cm³ of water, dried over magnesium sulphate, filtered and concentrated to dryness under reduced pressure (2.7 kPa). The residue is chromatographed on an alumina column (diameter 3.6 cm, height 31 cm), eluting under a nitrogen pressure of 0.1 bar with a dichloromethane and methanol mixture (95/5 by volume) and collecting fractions of 50 cm³. Fractions 5 to 30 are pooled and concentrated to dryness under reduced pressure (2.7 kPa). The solid obtained is washed with isopropyl oxide, drained and dried. 1.4 g of (3aR,4S,7aR)-7,7-diphenyl-2-[1-imino-2-(2-methoxyphenyl)ethyl]-4-perhydroisoindolol are obtained in the form of white crystals; melting point 105° C., with decomposition.

The present invention also relates to pharmaceutical compositions consisting of a product of general formula (I) or a salt, when these exist, optionally in combination with any other pharmaceutically compatible product, which may be inert or physiologically active. The compositions according to the invention may be used parenterally, orally, rectally or topically.

The sterile compositions for parenteral administration which may be used in particular in the form of perfusions are preferably aqueous or nonaqueous solutions, suspensions or emulsions. Water, propylene glycol, polyethylene glycol, vegetable oils, in particular olive oil, organic esters for injections, for example ethyl oleate or other suitable organic solvents may be used as solvent or vehicle. These compositions may also contain adjuvants, in particular wetting, isotonizing, emulsifying, dispersing and stabilizing agents. Sterilization may be performed in a number of ways, for example by asepticizing filtration, by incorporating sterilizing agents into the composition, by irradiation or by heating. They may also be prepared in the form of sterile solid compositions which may be dissolved at the time of use in a sterile medium for injection.

The compositions for rectal administration are suppositories or rectal capsules which contain, in addition to the active product, excipients such as cacao butter, semisynthetic glycerides or polyethylene glycols.

Tablets, pills, powders or granules may be used as solid compositions for oral administration. In these compositions, the active product according to the invention (optionally combined with another pharmaceutically compatible product) is mixed with one or more inert diluents or adjuvants such as sucrose, lactose or starch. These compositions may also comprise substances other than diluents, for example a lubricant such as magnesium stearate.

Emulsions which are pharmaceutically acceptable, solutions, suspensions, syrups and elixirs containing inert diluents such as water or paraffin oil may be used as liquid compositions for oral administration. These compositions may also comprise substances other than diluents, for example wetting, sweetening or flavoring products.

The compositions for topical administration may be for example creams, pomades or lotions.

In human therapy, the products according to the invention may be particularly useful in the treatment of pain of traumatic, post-surgical, menstrual, or cephalic origin, in the treatments of anxiety, psychoses, Parkinson's disease, schizophrenia and Alzeimer's disease, in muscle-relaxant treatment, in the treatment of spasmodic, painful and inflammatory manifestations of the digestive tracts (ulcerative colitis, irritable colon syndrome, Crohn's disease), of the urinary tracts (cystitis) and of the respiratory tracts (asthma, rhinitis) or in gynaecology and in the treatment of migraines. The new isoindole derivatives are also useful in the treatment of rheumatoid arthritis and in disorders due to the perturbation of the immune system, in the treatments of dermatological inflammations such as psoriasis, herpes, urticarias, eczemas, photodermatitis and in eye or dental inflammatory disorders.

The products according to the invention may also find an application in the treatments of cardiovascular disorders such as hypotension, or in the treatment of disorders associated with poor regulation of growth (dwarfism, hypotrophies resulting from chronic childrens diseases, osteoporosis, development of grafts).

The doses depend on the desired effect and on the duration of treatment. For an adult, they are generally between 0.25 and 1500 mg daily in graded doses.

Generally, the physician will determine the dosage which he judges to be most appropriate according to the age, the weight and all the other factors specific to the individual to be treated.

The following examples, given with no limitation being implied, illustrate compositions according to the invention.

Example A

Tablets of active product having the following composition are prepared according to the usual technique:

| | |
|---|---|
| (3aR,7R,7aR)-2-{{[3-(1-Pyrrolidinyl)-2-propoxy]phenyl}acetyl}-4,4-diphenyl-7-fluoro-4-perhydroisoindole | 25 mg |
| Starch | 83 mg |
| Silica | 30 mg |
| Magnesium stearate | 3 mg |

Example B

Tablets of active product having the following composition are prepared according to the usual technique:

| | |
|---|---|
| (3aR,7R,7aR)-4,4-Diphenyl-7-fluoro-2-[(S)-2-(2-methoxyphenyl)propionyl]-perhydroisoindole | 25 mg |
| Starch | 83 mg |
| Silica | 30 mg |
| Magnesium stearate | 3 mg |

We claim:
1. Perhydroisoindole derivatives of formula:

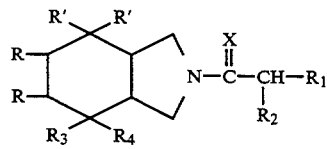

in which
the R radicals are identical and represent hydrogen atoms or together form a bond,
the symbols R' are identical and they represent phenyl radicals which are optionally substituted in position 2 or 3 by a halogen atom or by a methyl radical,
the symbol X represents an oxygen atom or an NH radical,
the symbol $R_1$ represents a phenyl radical which is optionally substituted by one halogen atom or hydroxyl or alkyl radical which may be optionally substituted by halogen atoms, amino, alkylamino or dialkylamino radicals, an alkoxy or alkylthio radical which may be optionally substituted by a hydroxyl, amino, alkylamino or dialkylamino radical which in turn is optionally substituted by a phenyl, hydroxyl or amino radicals, or by dialkylamino radicals whose alkyl parts form with the nitrogen atom to which they are attached, a heterocycle with 5 to 6 members which may contain another heteroatom chosen from oxygen, sulphur or nitrogen, optionally substituted by an alkyl, hydroxyl or hydroxyalkyl radical, or which is substituted by an amino, alkylamino or dialkylamino radical whose alkyl parts may form with the nitrogen atom to which they are attached, a heterocycle as defined above; or $R_1$ represents a cyclohexadienyl, naphthyl or a saturated or unsaturated, mono- or polycyclic heterocyclic radical containing 5 to 9 carbon atoms and at least one heteroatom chosen from oxygen, nitrogen or sulphur, the symbol $R_2$ represents a hydrogen or halogen atom or a hydroxyl, alkyl, aminoalkyl, alkylaminoalkyl, dialkylaminoalkyl, alkoxy, alkylthio, acyloxy, carboxyl, alkoxycarbonyl, dialkylaminoalkoxycarbonyl, benzyloxycarbonyl, amino, acylamino or alkoxycarbonylamino radical, the symbol $R_3$ represents a halogen atom or a hydroxyl radical, and the symbol $R_4$ represents a hydrogen atom or a halogen atom, the alkyl and acyl radicals being linear or branched and containing 1 to 4 carbon atoms, in its stereoisomeric forms or mixture thereof, as well as its salts when these exist.

2. A perhydroisoindole derivative according to claim 1, wherein
the radicals R are hydrogen atoms,
the symbols R' are phenyl radicals,
the symbol X represents an oxygen atom or an NH radical,
the symbol $R_1$ represents a phenyl radical which is optionally substituted by an alkoxy radical which may be optionally substituted by a dialkylamino radical or a dialkylamino radical whose alkyl parts form with the nitrogen atom to which they are attached, a heterocycle with 5 to 6 members, or the alkoxy is substituted by a dialkylamino radical whose alkyl parts may form with the nitrogen atom to which they are attached, a heterocycle with 5 to 6 members,
the symbol $R_2$ represents a hydrogen atom or an alkyl radical,
the symbol $R_3$ represents a fluorine or chlorine atom or a hydroxyl radical, and
the symbol $R_4$ represents a hydrogen atom or, together with $R_3$, represents a fluorine atom, the abovementioned alkyl radicals being linear or branched and containing 1 to 4 carbon atoms, in its stereoisomeric forms or mixtures thereof, as well as its salts when these exist.

3. 2-{{[3-(1-Pyrrolidinyl)-2-propoxy]phenyl-}acetyl}-4,4-diphenyl-7-fluoroperhydroisoindole in its stereoisomeric forms or mixtures thereof, as well as its salts.

4. 4,4-Diphenyl-7-fluoro-2-[(S)-2-(2-methoxyphenyl)-propionyl]perhydroisoindole in its stereoisomeric forms or mixtures thereof.

5. 2-}[2-(3-Dimethylaminopropoxy)phenyl]acetyl}-4,4-diphenyl-7-fluoroperhydroisoindole in its stereoisomeric forms or mixtures thereof, as well as its salts.

6. 7,7-Diphenyl-2-[(S)-2-(2-methoxyphenyl)propionyl]-4-perhydroisoindolol in its stereoisomeric forms or mixtures thereof.

7. 2-[(2-Methoxyphenyl)acetyl]-4,4-diphenyl-7-fluoroperhydroisoindole in its stereoisomeric forms or mixtures thereof.

8. Pharmaceutical composition comprising at least one product according to claim 1, in a pure state or combined with one or more compatible and pharmaceutically acceptable adjuvants or diluents.

9. A method of antagonizing the effects of substance P comprising administering to a patient in need thereof an effective amount of a perhydroisoindole derivative as claimed in claim 1.

* * * * *

UNITED STATES PATENT AND TRADEMARK OFFICE
CERTIFICATE OF CORRECTION

PATENT NO. : 5,451,601
DATED : September 19, 1995
INVENTOR(S) : Daniel ACHARD et al.

It is certified that error appears in the above-indentified patent and that said Letters Patent is hereby corrected as shown below:

On the title page,
  item [73] Assignee,    Line 8 "Lyons" should read --Lyon--.

Claim 3, Column 38, Line 62 "propoxyl]phenyl-}ace-" should read --propoxy]phenyl}ace---.

Claim 5, Column 39, Line 1 "2-}" should read --2-{--.

Signed and Sealed this

First Day of October, 1996

BRUCE LEHMAN

Attest:

Attesting Officer

Commissioner of Patents and Trademarks